United States Patent
Malhi et al.

(10) Patent No.: US 9,168,197 B2
(45) Date of Patent: Oct. 27, 2015

(54) VASCULAR COMPRESSION SYSTEM

(71) Applicant: Covidien LP, Mansfield, MA (US)

(72) Inventors: Arnaz Malhi, Watertown, MA (US);
Manish Deshpande, Canton, MA (US);
Steve Nardi, Taunton, MA (US);
Premnarayan Ganapathy, Brookline, MA (US); Anmol Nagre, Watertown, MA (US)

(73) Assignee: Covidien LP, Mansfield, MA (US)

( * ) Notice: Subject to any disclaimer, the term of this patent is extended or adjusted under 35 U.S.C. 154(b) by 609 days.

(21) Appl. No.: 13/630,628

(22) Filed: Sep. 28, 2012

(65) Prior Publication Data
US 2014/0094726 A1 Apr. 3, 2014

(51) Int. Cl.
*A61H 9/00* (2006.01)
*A61F 13/08* (2006.01)

(52) U.S. Cl.
CPC *A61H 9/00* (2013.01); *A61F 13/08* (2013.01); *A61H 9/0078* (2013.01); *A61H 2201/164* (2013.01); *A61H 2201/165* (2013.01); *A61H 2201/5002* (2013.01); *A61H 2201/5058* (2013.01); *A61H 2201/5071* (2013.01); *A61H 2201/5084* (2013.01); *A61H 2205/10* (2013.01); *A61H 2205/12* (2013.01)

(58) Field of Classification Search
CPC ......... A61H 9/00; A61H 9/007; A61H 9/005; A61H 9/0078–9/0092; A61H 2009/00; A61H 2009/005; A61H 2201/5056; A61H 2201/50–2201/5007; A61H 2205/10–2205/125; A61H 2209/00
See application file for complete search history.

(56) References Cited

U.S. PATENT DOCUMENTS

| | | | |
|---|---|---|---|
| 4,773,397 A * | 9/1988 | Wright et al. | 601/151 |
| 4,986,260 A | 1/1991 | Iams et al. | |
| 5,031,604 A * | 7/1991 | Dye | 601/152 |
| 5,443,440 A | 8/1995 | Tumey et al. | |
| 5,517,999 A | 5/1996 | Newell | |
| 5,855,589 A | 1/1999 | McEwen et al. | |
| 6,001,119 A | 12/1999 | Hampson et al. | |
| 6,007,559 A | 12/1999 | Arkans | |
| 6,544,202 B2 | 4/2003 | McEwen et al. | |
| 7,204,809 B2 | 4/2007 | Hung | |
| 7,270,642 B2 | 9/2007 | Ouchene et al. | |
| 2001/0000262 A1 | 4/2001 | McEwen et al. | |
| 2009/0260639 A1 * | 10/2009 | Hsu et al. | 128/888 |
| 2012/0022416 A1 * | 1/2012 | Munoz | 601/152 |

* cited by examiner

*Primary Examiner* — Rachel Young
(74) *Attorney, Agent, or Firm* — John Paul Mello, Esq.

(57) ABSTRACT

A vascular compression system includes a compression garment and a controller for compressing a body part of a person. In some embodiments, the compression garment is a foot cuff or a leg sleeve. The controller inflates compression garment apparatus includes a compression garment and a pressurizer. The pressurizer has instructions for executing cyclic compression cycles for applying intermittent compression therapy to the body part. Each compression cycle includes an inflation phase and a vent phase. At least one of the inflation phases includes a pre-fill step and a therapeutic step. In the pre-fill step, gas pressure in the inflatable chamber may be increased at a reduced rate, and in the therapeutic step, the gas pressure in the inflatable chamber may be increased at a rapid rate.

21 Claims, 26 Drawing Sheets

VASCULAR COMPRESSION SYSTEM

FIELD OF THE INVENTION

The present invention is directed generally to compression of a body part of a person, and more particularly to a vascular compression system for enhancing flow of bodily fluid in the body part.

BACKGROUND OF THE INVENTION

Among concerns for generally immobile persons are medical conditions that form blood clots, such as deep vein thrombosis (DVT) and peripheral edema. Such persons include those undergoing surgery, anesthesia, and extended periods of bed rest. These blood clotting conditions generally occur in the deep veins of the lower extremities and/or pelvis. Veins such as the iliac, femoral, popliteal, and tibial veins return deoxygenated blood to the heart. When blood circulation in these veins is retarded due to illness, injury, or inactivity, there is a tendency for blood to accumulate or pool. A static pool of blood may lead to a blood clot, which can interfere with cardiovascular circulation. More seriously, the blood clot can break loose and migrate. A pulmonary embolus, which may be life threatening, can form if the blood clot blocks a pulmonary artery.

Vascular compression systems are used to promote flow of bodily fluid. For example, conventional vascular compression systems include a compression garment fluidly connected to a controller that cyclically inflates the compression garment. The cyclical inflation of the compression garment enhances blood circulation and decreases the likelihood of DVT. Some compression garments are adapted for application to a foot of a person for compressing the foot. Other compression garments are adapted for application to a leg of a person for compressing the leg. In some instances, compression garments include a foot portion and a leg portion. In general, conduits are provided for fluidly connecting the compression garment to the controller. Some vascular compression systems include portable controllers that are much smaller and mountable on the compression garment, so the patient is not tethered to a device by tubing that restricts motion and may become tangled. Portable compression systems are believed to enhance patient compliance due to convenience of use.

Conventional controllers tend to create a fair amount of noise when inflating the compression garment. In general, efficacious compression therapy requires inflation of the compression garment at rapid flow rates. Conventional controllers generally include pressurizers (e.g., pumps) for generating pressurized air for inflating compression garments, and such pressurizers tend to create noise when generating the pressurized air. Moreover, the pressurized air tends to create noise as it enters inflatable chambers on the compression garment.

SUMMARY OF THE INVENTION

In a first aspect, the present invention includes a controller for use with a compression garment for imparting compression therapy on a body part of a person. The compression garment includes at least one inflatable chamber and a port permitting inflation and deflation of the inflatable chamber. The controller includes a source of pressurized gas operatively connectable in fluid communication with the inflatable chamber of the compression garment. The source of pressurized gas is adapted for selectively pressurizing the inflatable chamber by increasing gas pressure in the inflatable chamber to provide compression therapy to the body part. The controller also includes a control system operatively connected to the source of pressurized gas and adapted for controlling operation of the source of pressurized gas. The control system includes a tangible storage medium having instructions for executing successive compression cycles to impart intermittent compression therapy to the body part. Each compression cycle includes an inflation phase during which the control system directs pressurized gas to the inflatable chamber and a vent phase after the inflation phase during which the control system permits gas to vent from the inflatable chamber. The control system has instructions to execute at least one of the inflation phases in accordance with the following steps: in a first step, increasing the gas pressure in the inflatable chamber to no more than about 20 mmHg in no less than about 0.5 seconds; and in a second step after the first step, increasing the gas pressure in the inflatable chamber to at least about 120 mmHg in no more than about 2 seconds.

In said first aspect, in the first step, increasing the gas pressure in the inflatable chamber to no more than about 20 mmHg may include increasing the gas pressure in the inflatable chamber to between about 2 mmHg to about 20 mmHg.

In said first aspect, in the second step, increasing the gas pressure in the inflatable chamber to at least about 120 mmHg may include increasing the gas pressure in the inflatable chamber to between about 120 mmHg to about 210 mmHg.

In said first aspect, the controller may be provided in combination with the compression garment, and the compression garment may include a foot cuff adapted for application to a foot of the person and for applying efficacious intermittent compression therapy to the foot.

In said first aspect, the source of pressurized gas may include first and second valves in parallel, and the control system may have instructions to, in the first step, deliver gas through the first valve to the inflatable chamber and, in the second step, deliver gas through the second valve to the inflatable chamber.

In said first aspect, the source of pressurized gas may include a valve having first and second valve positions, and the control system may have instructions to, in the first step, deliver gas through the valve in the first valve position to the inflatable chamber and, in the second step, deliver gas through the valve in the second valve position to the inflatable chamber.

In said first aspect, the source of pressurized gas may include a variable speed pressurizer, and the control system may have instructions to, in the first step, operate the pressurizer at a first speed to deliver gas to the inflatable chamber and, in the second step, operate the pressurizer at a second speed greater than the first speed to deliver gas to the inflatable chamber.

In said first aspect, the control system may have instructions for executing the first and second steps for the inflation phase of selected compression cycles only when high flow requirements exist.

In said first aspect, the control system may have instructions for executing pressure-based inflation control during the first step and for executing timing-based inflation control during the second step.

In a second aspect, the present invention includes a controller for use with a compression garment for imparting compression therapy on a body part of a person. The compression garment includes at least one inflatable chamber and a port permitting inflation and deflation of the inflatable chamber. The controller includes a source of pressurized gas operatively connectable in fluid communication with the inflatable chamber of the compression garment. The source of pressurized gas is adapted for selectively pressurizing the inflatable chamber by increasing gas pressure in the inflatable chamber to provide compression therapy to the body part. The controller also includes a control system operatively connected to the source of pressurized gas and adapted for controlling operation of the source of pressurized gas. The control system may include a tangible storage medium having instructions for executing successive compression cycles to impart intermittent compression therapy to the body part. Each compression cycle includes an inflation phase during which the control system directs pressurized gas to the inflatable chamber and a vent phase after the inflation phase during which the control system permits gas to vent from the inflatable chamber. The control system has instructions to execute at least one of the inflation phases in accordance with the following steps: in a first step, increasing the gas pressure in the inflatable chamber to no more than about 10 mmHg in no less than about 1.5 seconds; and in a second step after the first step, increasing the gas pressure in the inflatable chamber to at least about 35 mmHg in no more than about 4 seconds.

In said second aspect, in the first step, increasing the gas pressure in the inflatable chamber to no more than about 10 mmHg may include increasing the gas pressure in the inflatable chamber to between about 2 mmHg to about 10 mmHg.

In said second aspect, in the second step, increasing the gas pressure in the inflatable chamber to at least about 35 mmHg may include increasing the gas pressure in the inflatable chamber to between about 35 mmHg to about 65 mmHg.

In said second aspect, the controller may be provided in combination with the compression garment, and the compression garment may include a leg sleeve adapted for application to at least a portion of a leg of the person and for applying efficacious intermittent compression therapy to the leg.

In said second aspect, the at least one inflatable chamber may include a first inflatable chamber and a second inflatable chamber, and the control system may have instructions to execute both of the first and second steps with respect to each of the first and second inflatable chambers.

In said second aspect, the control system may have instructions to increase the gas pressure in the first inflatable chamber in the first step to a first maximum pressure, and the control system may have instructions to increase the gas pressure in the second inflatable chamber in the first step to a second maximum pressure less than the first maximum pressure.

In said second aspect, the control system may have instructions to increase the gas pressure in the first inflatable chamber in the second step to a first minimum pressure, and the control system may have instructions to increase the gas pressure in the second inflatable chamber in the second step to a second minimum pressure less than the first minimum pressure.

In said second aspect, the control system may have instructions to begin executing the first step for the first inflatable chamber before beginning to execute the first step for the second inflatable chamber.

In said second aspect, the control system may have instructions to begin executing the second step for the first inflatable chamber before beginning to execute the second step for the second inflatable chamber.

In said second aspect, the source of pressurized gas may include a variable speed pressurizer, and the control system may have instructions to, in the first step, operate the pressurizer at a first speed to deliver gas to the inflatable chamber and, in the second step, operate the pressurizer at a second speed greater than the first speed to deliver gas to the inflatable chamber.

In said second aspect, the control system may have instructions for executing the first and second steps for the inflation phase of selected compression cycles only when high flow requirements exist.

In said second aspect, the control system may have instructions for executing pressure-based inflation control during the first step and for executing timing-based inflation control during the second step.

In a third aspect, the present invention includes a controller for use with a compression garment for imparting compression therapy on a body part of a person. The compression garment includes at least one inflatable chamber and a port permitting inflation and deflation of the inflatable chamber. The controller includes a source of pressurized gas operatively connectable in fluid communication with the inflatable chamber of the compression garment. The source of pressurized gas is adapted for selectively pressurizing the inflatable chamber by increasing gas pressure in the inflatable chamber to provide compression therapy to the body part. The controller also includes a control system operatively connected to the source of pressurized gas and adapted for controlling operation of the source of pressurized gas. The control system includes a tangible storage medium having instructions for executing successive compression cycles to impart intermittent compression therapy to the body part. Each compression cycle includes an inflation phase during which the control system directs pressurized gas to the inflatable chamber and a vent phase after the inflation phase during which the control system permits gas to vent from the inflatable chamber. The control system has instructions to execute at least one of the inflation phases in accordance with the following steps: in a first step, increasing the gas pressure in the inflatable chamber to no more than about 20 mmHg by delivering gas from the source of pressurized gas to the inflatable chamber at a maximum flow rate of no more than about 20 LPM; and in a second step after the first step, increasing the gas pressure in the inflatable chamber to at least about 120 mmHg by delivering gas from the source of pressurized gas to the inflatable chamber at a minimum flow rate of at least about 50 LPM.

In said third aspect, in the first step, delivering gas from the source of pressurized gas to the inflatable chamber at a maximum flow rate of no more than about 20 LPM may include delivering gas to the inflatable chamber at a maximum flow rate of between about 3 LPM to about 20 LPM.

In said third aspect, in the first step, increasing the gas pressure in the inflatable chamber to no more than about 20 mmHg may include increasing the gas pressure in the inflatable chamber to between about 2 mmHg to about 20 mmHg.

In said third aspect, in the second step, increasing the gas pressure in the inflatable chamber to at least about 120 mmHg may include increasing the gas pressure in the inflatable chamber to between about 120 mmHg to about 210 mmHg.

In said third aspect, the controller may be provided in combination with the compression garment, and the compression garment may include a foot cuff adapted for application to a foot of a person and for applying efficacious intermittent compression therapy to the foot.

In said third aspect, the source of pressurized gas may include first and second valves in parallel, and the control system may have instructions to, in the first step, deliver gas through the first valve to the inflatable chamber and, in the second step, deliver gas through the second valve to the inflatable chamber.

In said third aspect, the source of pressurized gas may include a valve having first and second valve positions, and the control system may have instructions to, in the first step, deliver gas through the valve in the first valve position to the inflatable chamber and, in the second step, deliver gas through the valve in the second valve position to the inflatable chamber.

In said third aspect, the source of pressurized gas may include a variable speed pressurizer, and the control system may have instructions to, in the first step, operate the pressurizer at a first speed to deliver gas to the inflatable chamber and, in the second step, operate the pressurizer at a second speed greater than the first speed to deliver gas to the inflatable chamber.

In said third aspect, the control system may have instructions for executing the first and second steps for the inflation phase of selected compression cycles only when high flow requirements exist.

In a fourth aspect, the present invention includes a controller for use with a compression garment for imparting compression therapy on a body part of a person. The compression garment includes at least one inflatable chamber and a port permitting inflation and deflation of the inflatable chamber. The controller includes a source of pressurized gas operatively connectable in fluid communication with the inflatable chamber of the compression garment. The source of pressurized gas is adapted for selectively pressurizing the inflatable chamber by increasing gas pressure in the inflatable chamber to provide compression therapy to the body part. The controller also includes a control system operatively connected to the source of pressurized gas and adapted for controlling operation of the source of pressurized gas. The control system includes a tangible storage medium having instructions for executing successive compression cycles to impart intermittent compression therapy to the body part. Each compression cycle includes an inflation phase during which the control system directs pressurized gas to the inflatable chamber and a vent phase after the inflation phase during which the control system permits gas to vent from the inflatable chamber. The control system has instructions to execute at least one of the inflation phases in accordance with the following steps: in a first step, increasing the gas pressure in the inflatable chamber to no more than about 10 mmHg by delivering gas from the source of pressurized gas to the inflatable chamber at a maximum flow rate of no more than about 1.0×LPM; and in a second step after the first step, increasing the gas pressure in the inflatable chamber to at least about 35 mmHg by delivering gas from the source of pressurized gas to the inflatable chamber at a minimum flow rate of at least about 2.0×LPM.

In said fourth aspect, in the first step, delivering gas from the source of pressurized gas to the inflatable chamber at a maximum flow rate of no more than about 1.0×LPM may include delivering gas to the inflatable chamber at a maximum flow rate of between about 0.25×LPM to about 1.0×LPM.

In said fourth aspect, in the first step, increasing the gas pressure in the inflatable chamber to no more than about 10 mmHg may include increasing the gas pressure in the inflatable chamber to between about 2 mmHg to about 10 mmHg.

In said fourth aspect, in the second step, increasing the gas pressure in the inflatable chamber to at least about 35 mmHg may include increasing the gas pressure in the inflatable chamber to between about 35 mmHg to about 65 mmHg.

In said fourth aspect, the controller may be provided in combination with the compression garment, and the compression garment may include a leg sleeve adapted for application to at least a portion of a leg of a person and for applying efficacious intermittent compression therapy to the leg.

In said fourth aspect, the at least one inflatable chamber may include a first inflatable chamber and a second inflatable chamber, and the control system may have instructions to execute both of the first and second steps with respect to each of the first and second inflatable chambers.

In said fourth aspect, the control system may have instructions to increase the gas pressure in the first inflatable chamber in the first step to a first maximum pressure, and the control system may have instructions to increase the gas pressure in the second inflatable chamber in the first step to a second maximum pressure less than the first maximum pressure.

In said fourth aspect, the control system may have instructions to increase the gas pressure in the first inflatable chamber in the second step to a first minimum pressure, and the control system may have instructions to increase the gas pressure in the second inflatable chamber in the second step to a second minimum pressure less than the first minimum pressure.

In said fourth aspect, the control system may have instructions to begin executing the first step for the first inflatable chamber before beginning to execute the first step for the second inflatable chamber.

In said fourth aspect, the control system may have instructions to begin executing the second step for the first inflatable chamber before beginning to execute the second step for the second inflatable chamber.

In said fourth aspect, the source of pressurized gas may include a variable speed pressurizer, and the control system may have instructions to, in the first step, operate the pressurizer at a first speed to deliver gas to the inflatable chamber and, in the second step, operate the pressurizer at a second speed greater than the first speed to deliver gas to the inflatable chamber.

In said fourth aspect, the control system may have instructions for executing the first and second steps for the inflation phase of selected compression cycles only when high flow requirements exist.

In a fifth aspect, the present invention includes a controller for use with a compression garment for imparting compression therapy on a body part of a person. The compression garment includes at least one inflatable chamber and a port permitting inflation and deflation of the inflatable chamber. The controller includes a source of pressurized gas operatively connectable in fluid communication with the inflatable chamber of the compression garment. The source of pressurized gas includes a compressor being adapted for selectively pressurizing the inflatable chamber by increasing gas pressure in the inflatable chamber to provide compression therapy to the body part and a control system operatively connected to the compressor and adapted for controlling operation of the compressor. The control system includes a tangible storage medium having instructions for executing successive compression cycles to impart intermittent compression therapy to the body part. Each compression cycle includes an inflation phase during which the control system directs pressurized gas to the inflatable chamber and a vent phase after the inflation phase during which the control system permits gas to vent from the inflatable chamber. The control system has instructions to execute at least one of the inflation phases in accordance with the following steps: in a first step, increasing the gas pressure in the inflatable chamber to no more than about 20 mmHg by controlling the compressor to run at a first speed; and in a second step after the first step, increasing the gas pressure in the inflatable chamber to at least about 120 mmHg by controlling the compressor to run at a second speed greater than the first speed.

In a sixth aspect, the present invention includes a controller for use with a compression garment for imparting compression therapy on a body part of a person. The compression garment includes at least one inflatable chamber and a port permitting inflation and deflation of the inflatable chamber. The controller includes a source of pressurized gas operatively connectable in fluid communication with the inflatable chamber of the compression garment. The source of pressurized gas is adapted for selectively pressurizing the inflatable chamber by increasing gas pressure in the inflatable chamber to provide compression therapy to the body part. The controller also includes a control system operatively connected to the source of pressurized gas and adapted for controlling operation of the source of pressurized gas. The control system includes a tangible storage medium having instructions for executing successive compression cycles to impart intermittent compression therapy to the body part. Each compression cycle includes an inflation phase during which the control system directs pressurized gas to the inflatable chamber and a vent phase after the inflation phase during which the control system permits gas to vent from the inflatable chamber. The control system has instructions to execute at least one of the inflation phases in accordance with the following steps: in a first step, increasing the gas pressure in the inflatable chamber to no more than about 20 mmHg by delivering gas from the source of pressurized gas to the inflatable chamber through a first orifice; and in a second step after the first step, increasing the gas pressure in the inflatable chamber to at least about 120 mmHg by delivering gas from the source of pressurized gas to the inflatable chamber through a second orifice larger than the first orifice.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
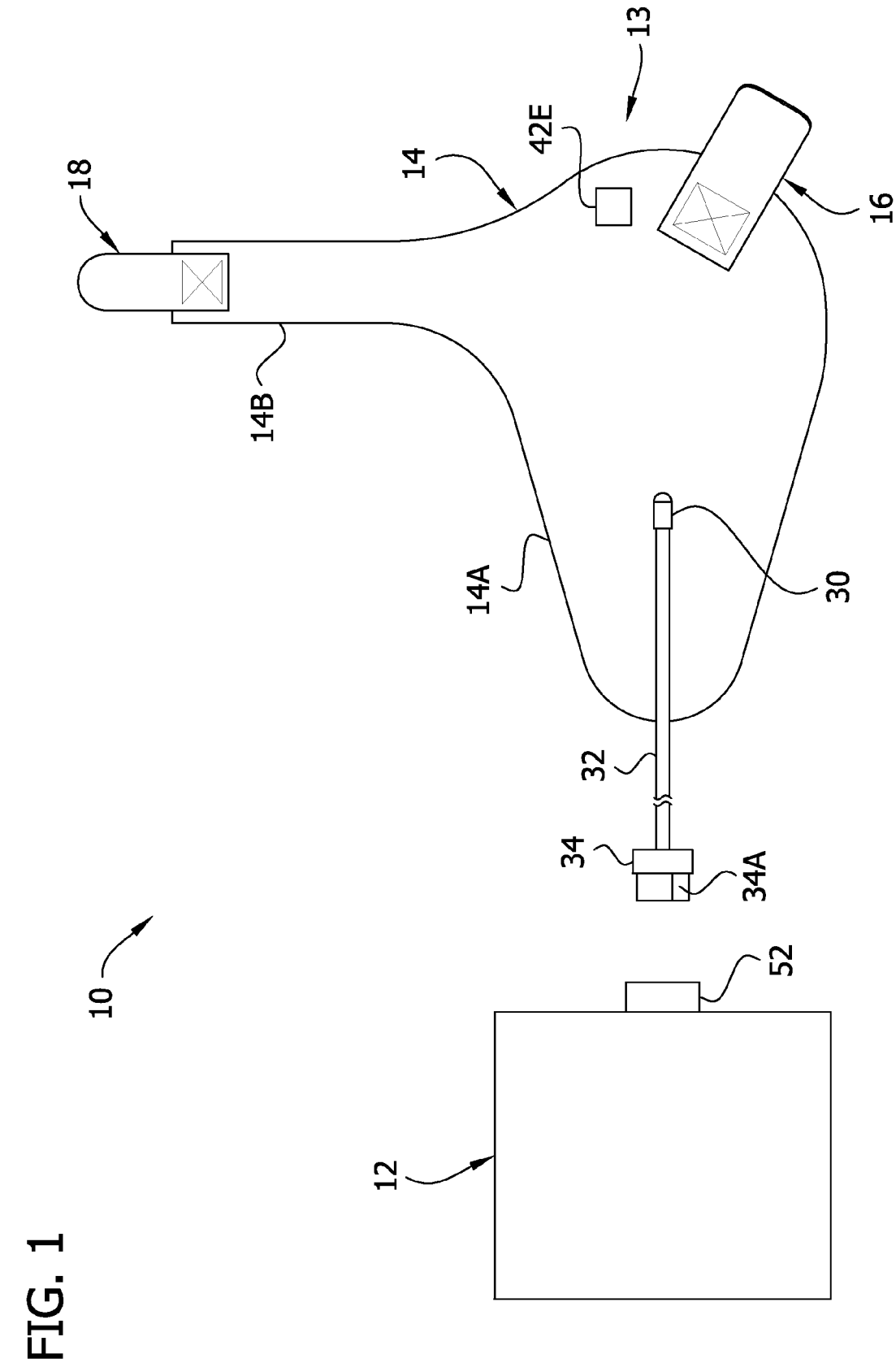
FIG. 1 is a schematic plan view of a compression system of the present invention, the compression system including a compression garment and a controller.
Figure 2:
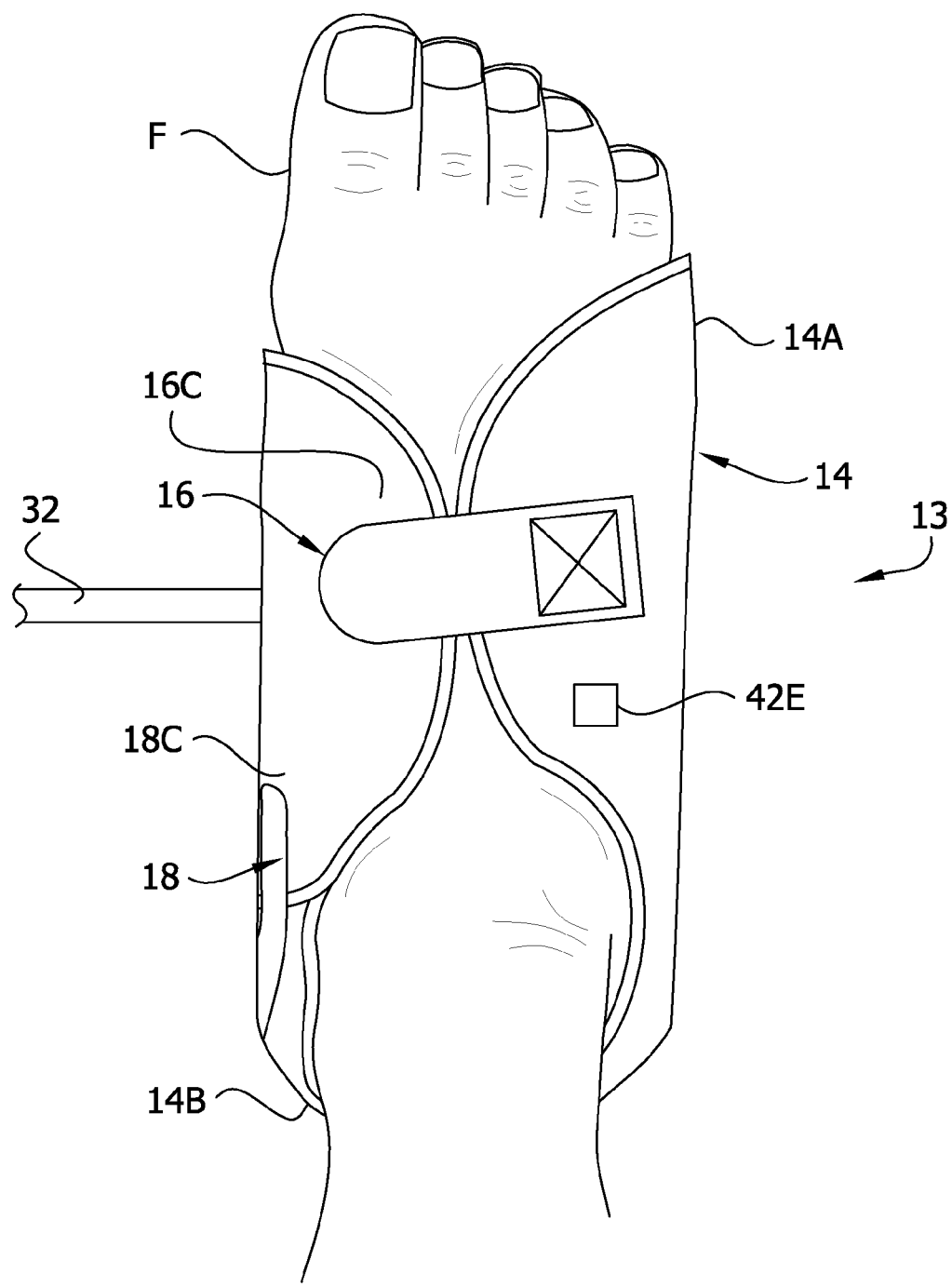
FIG. 2 is a top view of the compression garment as applied to a foot of a person.

Referring to FIG. 1, a first embodiment of a compression system of the present invention is generally indicated by the reference number 10. The compression system includes a controller 12 and a compression garment 13 adapted for compressing a body part. In particular, the illustrated compression garment 13 is a foot cuff 14 configured for compressing a foot F (FIG. 2). Compression garments having other sizes or shapes and compression garments adapted for compressing other body parts (e.g., a leg) or combinations of body parts (e.g., a foot and a leg) may be used without departing from the scope of the present invention.

Figure 3:
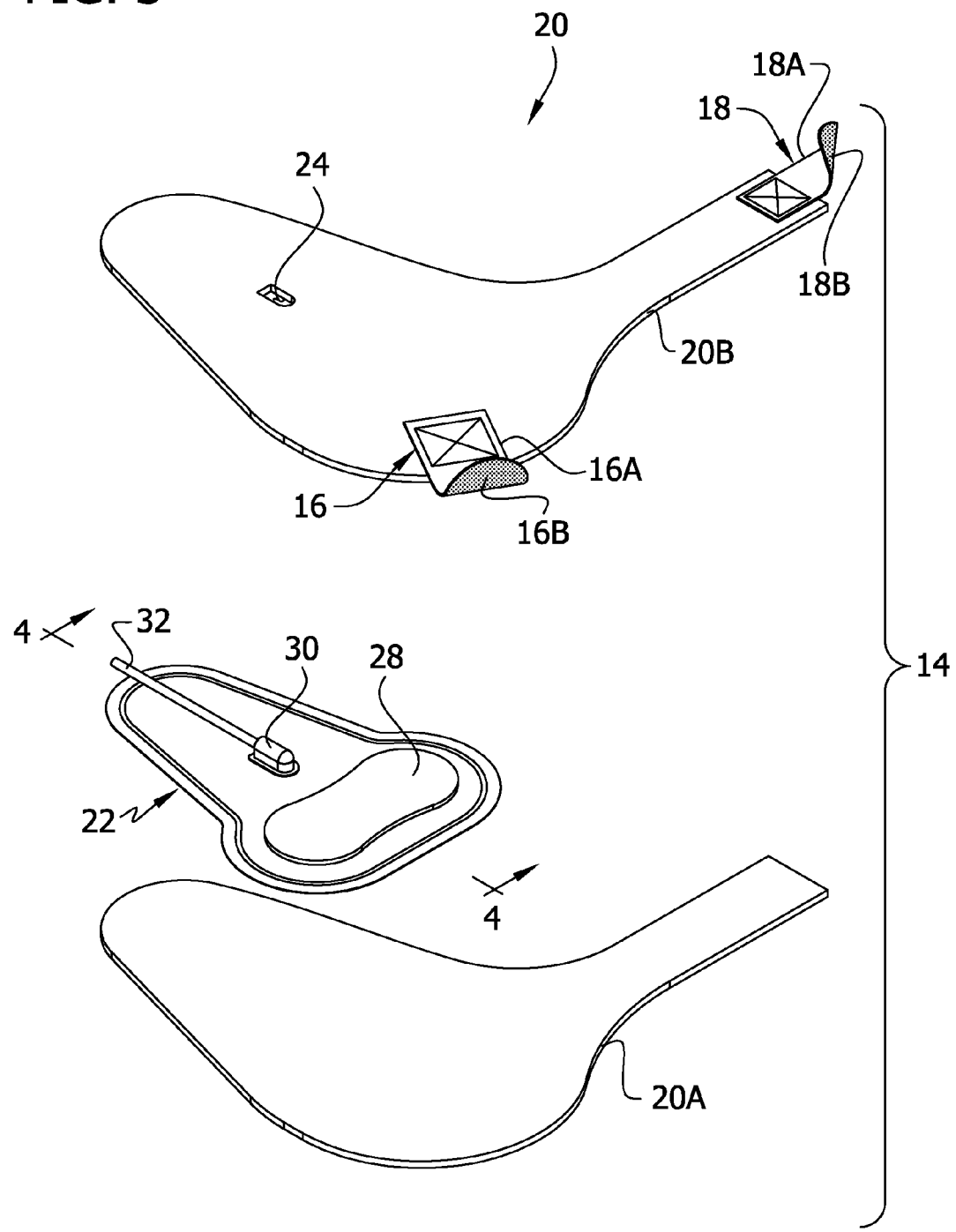
FIG. 3 is an exploded perspective of the compression garment.

As shown in FIG. 2, the foot cuff 14 is adapted for wrapping around the foot F, as is known by persons having ordinary skill in the art. The foot cuff 14 includes a main body 14A and an ankle strap 14B. In use, the main body 14A is positioned below the sole of the foot F and wrapped around the bridge of the foot, and the ankle strap 14B is wrapped behind the ankle. The foot cuff 14 is secured in this configuration using releasable fastening assemblies 16, 18 which in the illustrated embodiment comprise straps 16A, 18A having a surface of hook elements 16B, 18B (FIG. 3). The first fastening assembly 16 is provided on the main body 14A for fastening the main body in position wrapped around the foot F. The second fastening assembly 18 is provided on a free end of the ankle strap 14B for fastening the ankle strap in position wrapped behind the ankle. The surfaces of hook elements 16B, 18B are adapted for releasably fastening to loop fabric 16C, 18C provided on an outer surface of the foot cuff 14. It will be understood that the loop fabric can be a single piece of material forming substantially the entire outer surface of the foot cuff. Foot cuffs having other configurations and other fastening assemblies may be used without departing from the scope of the present invention.

The foot cuff 14 includes a cover 20 in the form of an inner (contact) cover layer 20A and an outer cover layer 20B. The inner and outer cover layers 20A, 20B are secured to one another along a line generally adjacent corresponding perimeters of the layers to define an interior space for receiving and substantially enclosing a bladder assembly, generally designated 22. The inner and outer cover layers 20A, 20B may be fixedly secured to one another, such as by heat welding, adhesives, sewing, or other suitable ways. Alternatively, the layers 20A, 20B may be releasably secured to one another. In use, the inner cover layer 20A is adjacent to the wearer's foot and the outer cover layer 20B is located farthest from the foot. As used herein, the terms "inner" and "outer" indicate relative positions of respective components and surfaces with respect to the skin of the wearer's body part when the compression garment is secured to the body part, and as such, an "inner" component or surface is more adjacent to the skin of the body part than an "outer" component or surface.

The inner and outer cover layers 20A, 20B may be made of various suitable materials. For example, the inner cover layer 20A may be fabricated from a chemically treated material, with wicking ability, for wicking moisture away from the skin. The inner and outer cover layers 20A, 20B may include various types of cloth or fabric material or various types of foam material. Other configurations of covers for the foot cuff may be used without departing from the present invention. Moreover, one or both of the cover layers 20A, 20B may be omitted without departing from the scope of the present invention.

Figure 4:
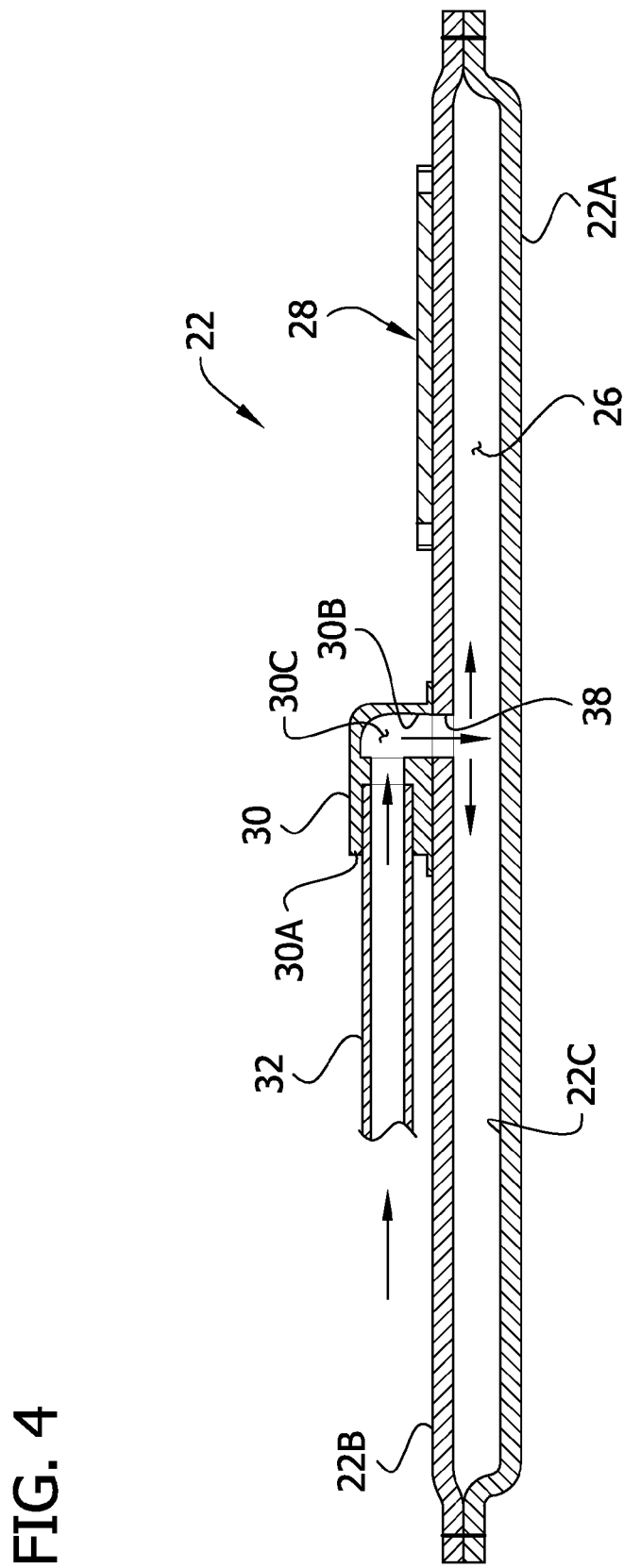
FIG. 4 is an enlarged section of a bladder assembly of the compression garment taken in the plane including line 4-4 in FIG. 3.

As shown in FIG. 3, the outer cover layer 20B includes an opening 24 for allowing passage of pressurized gas (e.g. air) to the bladder assembly 22. As shown in FIG. 4, the bladder assembly 22 comprises inner and outer bladder layers 22A, 22B defining an inflatable chamber 26 therebetween, a substantially rigid sole 28, and a port 30. The port 30 has a first opening 30A remote from the chamber 26 and a second opening 30B leading into the inflatable chamber 26. A flexible conduit 32 is provided for connecting the first opening 30A of the port 30 in fluid communication with the controller 12 for delivery of gas to the inflatable chamber 26.

As shown in FIG. 4, the inner and outer bladder layers 22A, 22B are positioned in face-to-face opposing relationship. The bladder layers 22A, 22B are desirably made of a flexible gas-impermeable material (e.g., PVC) and are joined together in a suitable manner (e.g., RF welding) to form the inflatable chamber 26. For example, the bladder layers 22A, 22B may be sealed together along a line adjacent to their peripheries to define the inflatable chamber 26. The bladder assembly 22 is positioned inside the cover 20 so a portion of the inflatable chamber 26 underlies the sole of the foot F when the foot cuff 14 is positioned on the foot. The inflatable chamber 26 is adapted for receiving and retaining pressurized gas for exerting compressive pressure on the foot F during successive or intermittent pressure application cycles. Bladder assemblies having other configurations and constructions may be used without departing from the scope of the present invention. For example, other ways of joining the bladder layers 22A, 22B include sewing, adhesive, and heat sealing may be used. Moreover, it is understood the bladder assembly 22 may have more than one inflatable chamber without departing from the scope of the present invention.

The sole 28 is a substantially rigid member positioned between the outer bladder layer 22B and the outer cover layer 20B. The sole 28 extends generally lengthwise along the bottom of the foot F when the foot cuff 14 is worn. The sole 28 provides a substantially rigid foundation which causes the inflatable chamber 26 to expand toward, instead of away from, the sole of the foot F. Other soles may be used, or the sole may be omitted, without departing from the scope of the present invention.

As shown in FIG. 4, in the illustrated embodiment, the port 30 is a right-angle or elbow port having a flow passage 30C. The port 30 may be made of any suitable material (e.g., molded plastic). The flow passage 30C extends from the first opening 30A to the second opening 30B to permit flow of gas from the conduit 32 to the inflatable chamber 26. The second opening 30B of the port 30 is connected to the outer bladder layer 22B (e.g., by heat sealing, RF welding, or adhesive) and is positioned in registration with a gas flow opening 38 in the outer bladder layer 22B. When the foot cuff 14 is assembled, the port 30 extends out of the opening 24 in the outer cover layer 20B. An end of the conduit 32 is connected to the first opening 30A (e.g., by heat sealing, RF welding, or adhesive), and a connector 34 (FIG. 1) is provided at an opposite end of the conduit 32 for connecting the inflatable chamber 26 in fluid communication with the controller 12. Ports having other configurations may be used without departing from the scope of the present invention. For example, the port 30 need not be a right-angle port, more than one port may be provided, and ports may be provided at other locations on the bladder assembly 22.

Gas entering the inflatable chamber 26 may create noise (pressure waves in an audible range) which is unpleasant to the person wearing the foot cuff 14, partially because the inflatable chamber is inflated repeatedly. Referring again to FIG. 4, the bladder assembly 22 includes an internal gas impingement surface 22C inside the inflatable chamber 26. The gas impingement surface 22C opposes the second opening 30B of the port 30. In the illustrated embodiment, the impingement surface 22C is the interior surface of the inner bladder layer 22A. When the inflatable chamber 26 is inflated, gas delivered to the inflatable chamber enters the chamber in the form of a gas jet from the second opening 30B of the port 30. The gas jet impinges against the gas impingement surface 22C, which may generate noise.

Persons having ordinary skill in the art understand it is desirable to minimize rise time to peak pressure in the inflatable chamber 26 in order to impart efficacious compression therapy, i.e., for moving bodily fluid such as blood. Conventional compression garments are inflated at a rapid flow rate to achieve peak pressure in sufficiently short time to accomplish adequate movement of blood. The rapid flow rate causes the gas jet to create excessive noise when it impinges against internal surfaces of the inflatable chamber such as the impingement surface. Moreover, the controller itself may generate excessive noise when operating to achieve such rapid flow rates.

Figure 5:
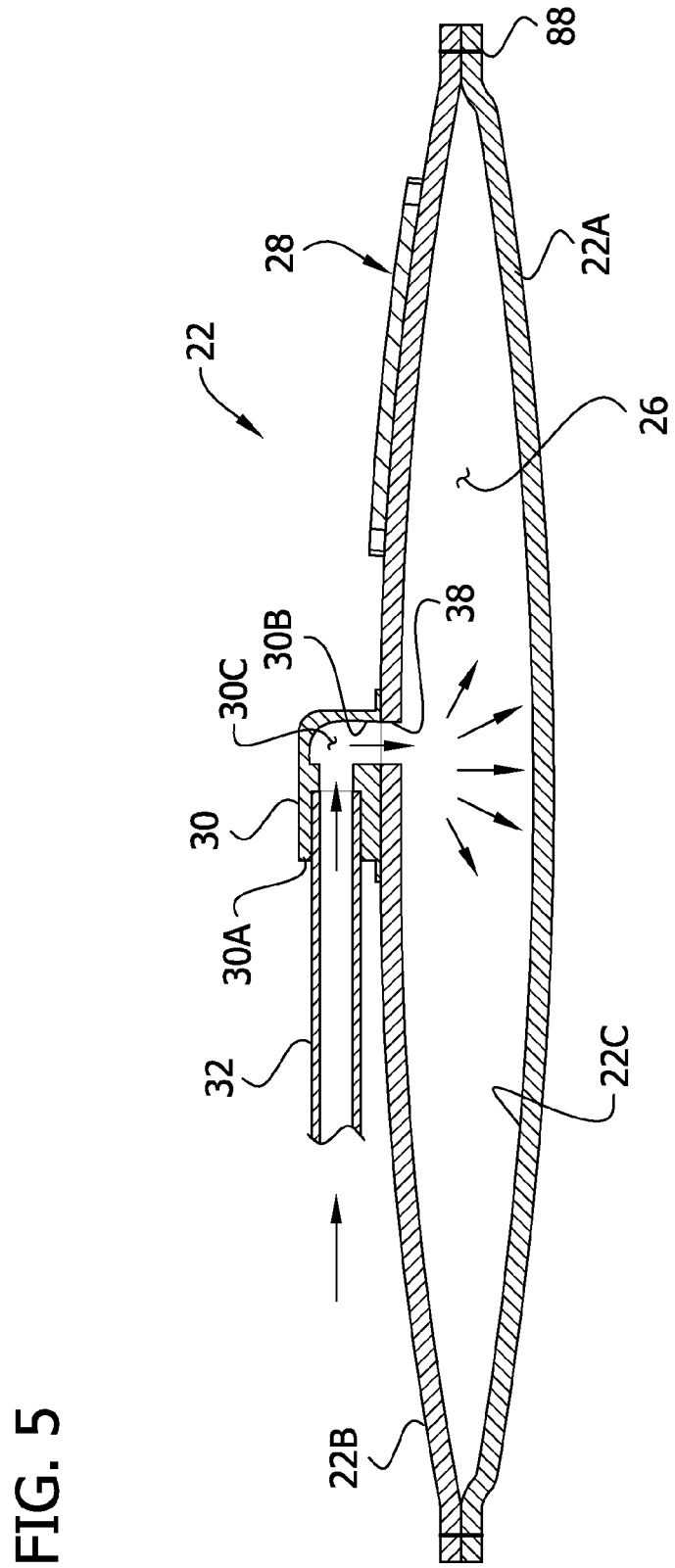
FIG. 5 is a view similar to FIG. 4 but showing the bladder assembly in a partially inflated configuration.

In conventional configurations, noise generation via impingement is generally greatest at the beginning of an inflation cycle and decreases as the inflatable chamber is inflated. As explained above, during inflation of the inflatable chamber 26, a jet of pressurized gas enters the inflatable chamber from the second opening 30B of the port 30. As the gas in the jet moves away from the port 30, the flow area of the gas increases and the velocity of the gas decreases. Before inflation begins, the inflatable chamber 26 may have a generally deflated configuration as shown in FIG. 4, with the impingement surface 22C relatively close to the second opening 30B of the port 30. When inflation begins, the gas jet impinges directly against a relatively small portion of the impingement surface 22C opposite the second opening 30B of the port 30 with relatively high velocity, creating noise. As gas accumulates in the inflatable chamber 26, the impingement surface 22C moves away from the second opening 30B of the port 30. For example, as shown in FIG. 5, when the inflatable chamber 26 is partially inflated, the impingement surface 22C is farther from the second opening 30B of the port 30 than in the generally deflated position. Gas entering the inflatable chamber 26 with the impingement surface 22C in this position produces less noise because the jet of pressurized gas impinges against a larger portion of the impingement surface 22C and strikes against the impingement surface with less velocity. Further inflation of the inflatable chamber 26 may move the impingement surface 22C even farther from the port second opening, such as to the position shown in FIG. 6, and result in generation of even less noise. As will be described below, aspects of the present invention are directed to managing flow of the gas jet into the inflatable chamber 26 for reducing noise generated during inflation.

Figure 6:
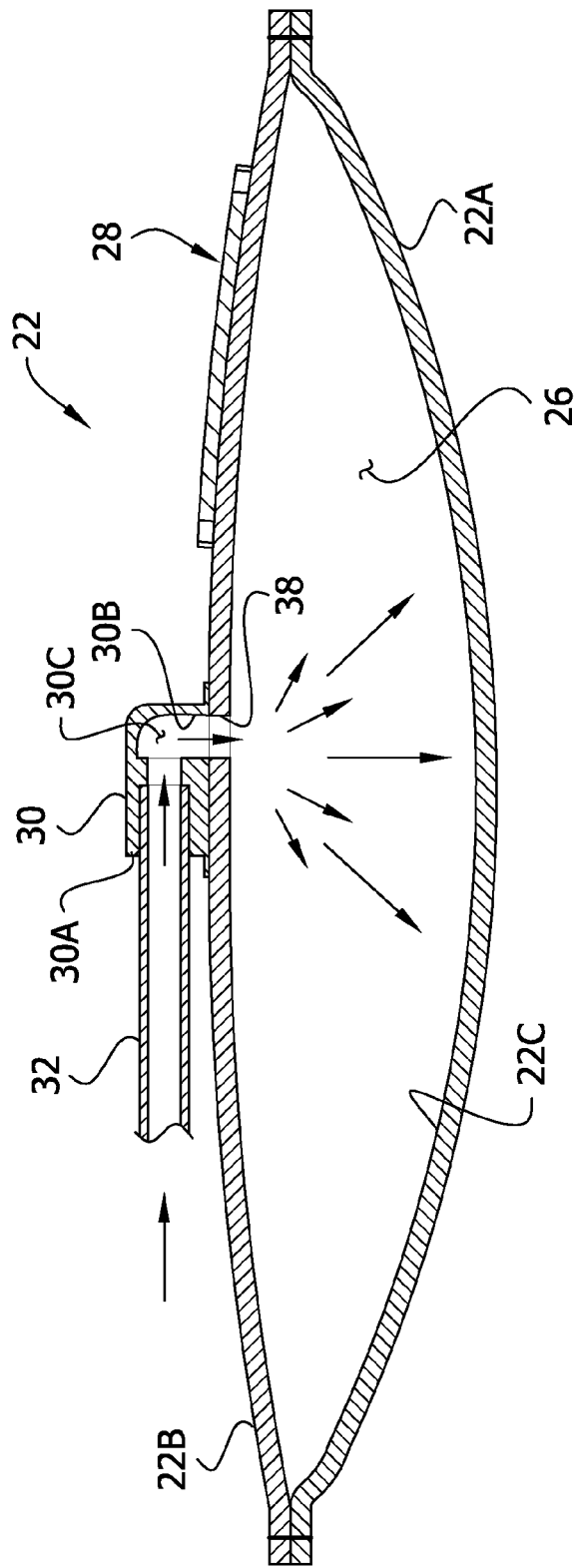
FIG. 6 is view similar to FIG. 4 but showing the bladder assembly in a fully inflated configuration.

The configurations of the bladder assembly 22 in the generally deflated, partially inflated, and fully inflated configurations in FIGS. 4-6 are provided by example and not limitation. It is understood the bladder assembly 22 and inflatable chamber 26 may have configurations other than shown when wrapped on a foot in use.

Figure 7:
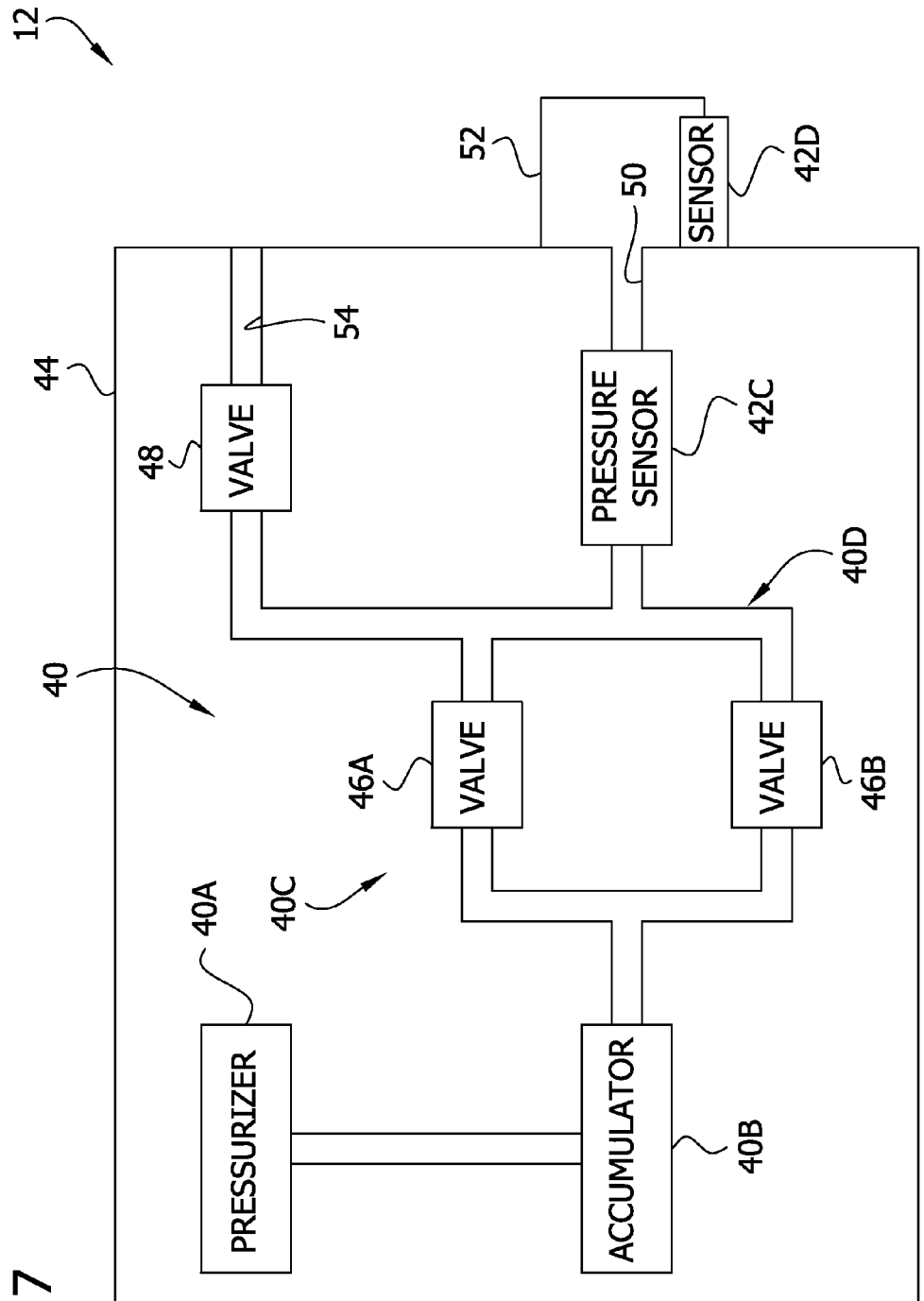
FIG. 7 is a schematic of the controller of FIG. 1.

Referring to FIG. 7, an exemplary embodiment of the controller 12 will now be described in further detail. In general, the controller 12 includes a source of pressurized gas, generally indicated by 40, and a control system, generally indicated by 42 (FIG. 8), for controlling delivery of gas to and from the inflatable chamber 26 of the foot cuff 14. The source of pressurized gas 40 and the control system 42 may be housed together in a housing 44. As shown schematically in FIG. 7, the source of pressurized gas 40 includes a pressurizer 40A, an accumulator 40B, valving 40C, and gas flow passaging 40D connecting respective components in fluid communication with each other. The pressurizer 40A may comprise any suitable pump or compressor adapted for pressurizing gas. The accumulator 40B is adapted for accumulating the pressurized gas. In the illustrated embodiment, the valving 40C includes first and second inflation valves 46A, 46B positioned in parallel along the gas flow passaging 40D and an exhaust valve 48 positioned downstream from the inflation valves. The gas flow passaging 40D includes a port 50 for delivering gas to and receiving gas from the inflatable chamber 26 of the foot cuff 14. A connector 52 is provided at the port 50 for operatively connecting the controller 12 in fluid communication with the foot cuff 14 via the connector 34 on the conduit 32 extending from the foot cuff 14. The gas flow passaging 40D also includes an exhaust 54 downstream from the exhaust valve 48 for exhausting or venting gas from the inflatable chamber 26.

In use, the pressurizer 40A generates pressurized gas which is stored in the accumulator 40B and selectively delivered to the inflatable chamber 26 through the first and second inflation valves 46A, 46B. Each inflation valve 46A, 46B has a closed position in which it prevents gas flow through the valve and an open position in which it permits gas to flow through the valve. The first valve 46A has a smaller flow area (e.g., a smaller orifice) than the second valve 46B. Thus, when the first and second valves 46A, 46B are in their respective open positions, the first valve 46A permits less gas flow than the second valve 46B. Gas is selectively vented from the inflatable chamber 26 via the exhaust valve 48 out of the exhaust 54.

Sources of pressurized gas configured other than illustrated or described herein may be used without departing from the scope of the present invention. For example, the accumulator 40B may be omitted, other valving arrangements may be used, and other configurations of flow passaging may be used. In another example, the pressurizer 40A could be omitted if a source of compressed air is available.

Figure 8:
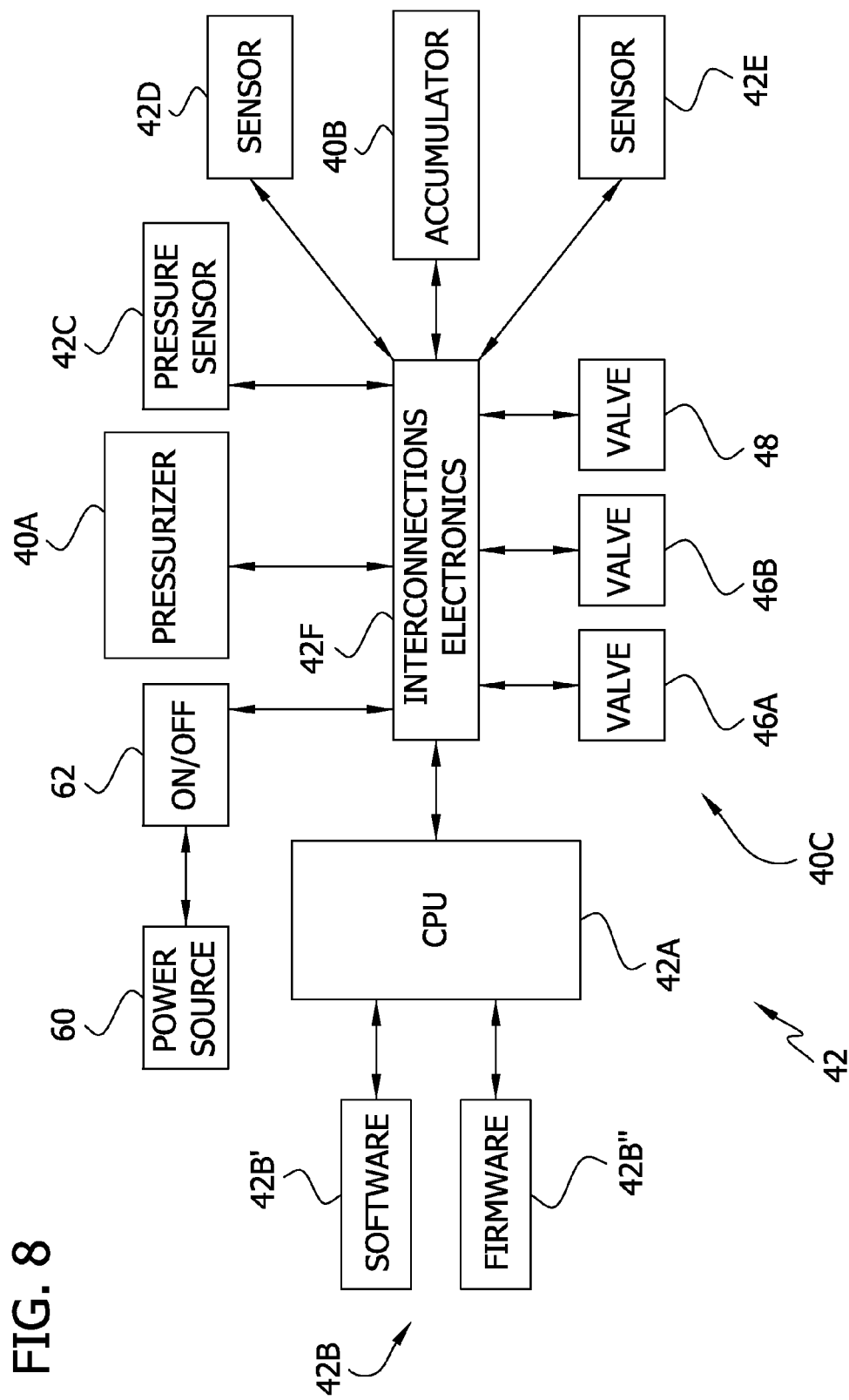
FIG. 8 is a schematic of a control system of the controller.

As shown schematically in FIG. 8, an embodiment of the control system 42 includes a central processing unit (CPU) 42A, a tangible storage medium 42B, a pressure sensor 42C, and two physical characteristic sensors 42D, 42E. The control system 42 is selectively energized by a power source 60 (e.g., a battery or utility power) by actuating an ON/OFF switch 62. The control system 42 also includes interconnections electronics 42F which operatively connect the other components of the control system and operatively connect the control system to the source of pressurized gas 40. The CPU 42A may be a microprocessor or the like. The tangible storage medium 42B may include forms of storage such as software 42B' and firmware 42B". The CPU 42A is adapted for reading and executing instructions stored in the storage medium 42B. The CPU 42A provides control signals via the interconnection electronics 42F to operate the source of pressurized gas 40. More specifically, the CPU 42A may provide control signals for operating the pressurizer 40A, the accumulator 40B, and/or the valving 40C to manage inflation and deflation of the inflatable chamber 26. For example, the interconnection electronics 42F transmit signals from the CPU 42A to the pressurizer 40A, accumulator 40B, and/or valving 40C wirelessly or via electrical or fiber optic lines. The pressure sensor 42C and physical characteristic sensors 42D, 42E may communicate with the CPU 42A, for example, wirelessly or via electrical or fiber optic lines.

The pressure sensor 42C senses gas pressure in the flow passaging 40D indicative of the gas pressure in the inflatable chamber 26 and generates signals which are communicated to the CPU 42A indicative of the sensed pressure. The physical characteristic sensors may include a first sensor 42D adapted for sensing a type of foot cuff 14 connected to the controller 12 and a second sensor 42E which is adapted for sensing a physical characteristic of the foot cuff 14 and/or the foot F. For example, the first sensor 42D may be provided on the controller connector 52 (FIG. 7) for sensing the type of foot cuff 14 (e.g., size) as indicated by an indicator 34A (FIG. 1) provided on the connector 34 of the foot cuff 12. Thus, this sensor 42D may indicate flow requirements for inflating the foot cuff 14. As shown in FIG. 1, the second sensor 42E may be provided on the foot cuff 14 in the form of an accelerometer or other suitable sensor for sensing physical characteristics such as orientation or movement of the foot cuff 14 or foot F. The second sensor 42E may indicate physical characteristics which increase the flow requirements to inflate the foot cuff 14 sufficiently to achieve efficacious compression therapy. Control systems having other configurations may be used without departing from the scope of the present invention.

The control system 42 is programmed for executing successive compression cycles to impart intermittent compression therapy to the foot F. For example, the software 42B' and/or firmware 42B" have instructions for executing the successive compression cycles. Each compression cycle includes an inflation phase during which the control system 42 directs pressurized gas from the source of pressurized gas to the inflatable chamber to increase gas pressure in the inflatable chamber 26 to a desired "peak" pressure to compress the foot F. Each compression cycle also includes a vent phase after the inflation phase during which the control system 42 permits gas to vent from the inflatable chamber 26 to decrease gas pressure in the inflatable chamber to relieve compression on the foot F. The compression cycles are executed one after another for a selected duration for imparting intermittent compression therapy to the foot F.

In one aspect of the present invention, the controller 12 is programmed to manage flow of gas into the inflatable chamber 26 to reduce the amount of noise generated during inflation of the inflatable chamber, among other advantages. In general, the controller 12 may be programmed for (i.e., the storage medium 42B has instructions for) inflating the inflatable chamber 26 at a first reduced flow rate or "pre-fill" flow rate before completing inflation of the inflatable chamber at a second rapid flow rate or "therapeutic" flow rate. The controller 12 begins inflation of the inflatable chamber 26 by increasing the gas pressure in the inflatable chamber at the pre-fill flow rate until the impingement surface 22C is moved at least some distance away from the second opening 30B of the port 30. In the embodiment illustrated in FIG. 7, the control system 42 may open the first inflation valve 46A (when the second inflation valve 46B is closed) to deliver gas to the inflatable chamber 26 through the first inflation valve 46A at the pre-fill flow rate. In other words, the first inflation valve 46A may be configured (e.g., have an appropriately sized orifice) to permit flow at the pre-fill flow rate when open. The pre-fill flow rate is less than the conventional rapid flow rate and thus creates less impingement noise than the conventional rapid flow rate. After the impingement surface 22C is moved away from the second opening 30B of the port 30, the controller 12 completes inflation of the inflatable chamber 26 by increasing the gas pressure in the inflatable chamber 26 at the therapeutic flow rate, which is greater than the pre-fill flow rate and which achieves peak pressure in a sufficiently minimal time to impart efficacious compression therapy. In the embodiment illustrated in FIG. 7, the control system 42 may open the second inflation valve 46B (when the first inflation valve 46A is closed) to deliver gas to the inflatable chamber 26 through the second inflation valve at the therapeutic flow rate. In other words, the second inflation valve 46B may be configured (e.g., have an appropriately sized orifice) to permit flow at the therapeutic flow rate when open. By managing the inflation of the inflatable chamber 26 in this way, less overall impingement noise is created, and in particular, less impingement noise is generated at the beginning of the inflation phase (during inflation at the pre-fill flow rate).

As explained above, the controller 12 may be programmed for executing successive compression cycles, each of which include an inflation phase and a deflation phase. To manage inflation of the inflatable chamber 26 to generate less noise as described above, the storage medium 42B may include appropriate instructions. In a first inflation phase example, the storage medium 42B may include instructions for increasing the gas pressure in the inflatable chamber 26 during the inflation phase in accordance with the following steps: (1) in a first step, increasing the gas pressure in the inflatable chamber 26 to no more than about a predetermined pre-fill pressure in no less than a predetermined pre-fill time; and (2) in a second step after the first step, increasing the gas pressure in the inflatable chamber 26 to at least about a predetermined therapeutic pressure in no more than a predetermined therapeutic time. In the first step, the predetermined pre-fill pressure may range in one embodiment from about 2 mmHg to 20 mmHg, and more desirably from about 5 mmHg to 12 mmHg. In the first step, the predetermined pre-fill time may range from about 0.5 seconds to 4 seconds, and more desirably from about 0.5 seconds to 1.5 seconds. In the second step, the predetermined therapeutic pressure may range in one embodiment from about 120 mmHg to about 210 mmHg, and more desirably from about 160 mmHg to 200 mmHg. In the second step, the predetermined therapeutic time may range in one embodiment from about 0.1 seconds to about 3 seconds, and more desirably from about 0.2 seconds to about 1 second.

Figure 9:
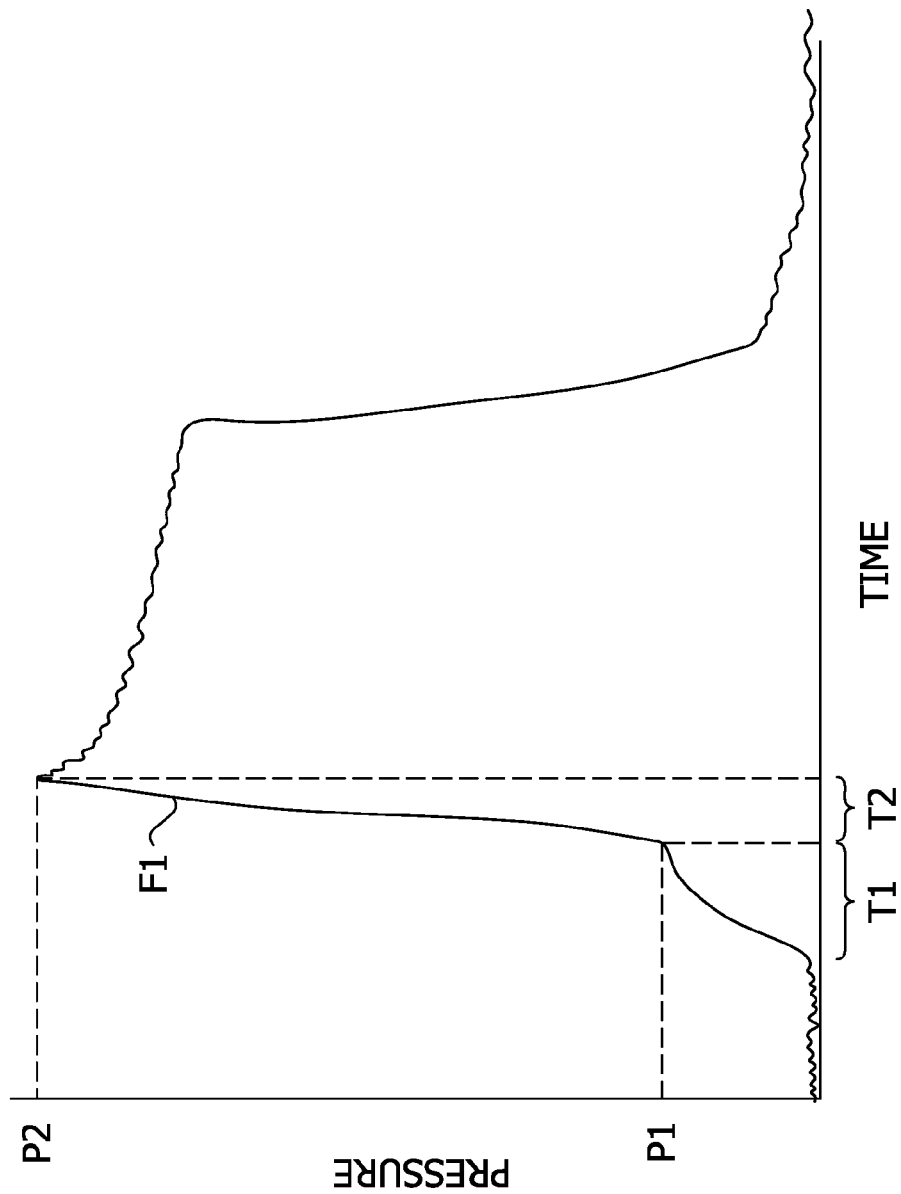
FIG. 9 is a graph showing an example pressure profile according to the present invention.

FIG. 9 illustrates a graph of a profile of pressure in the inflatable chamber 26 (represented by curve F1) during an example compression cycle according to the present invention. When the inflation phase begins, the pressure in the inflatable chamber 26 may be negligible or about zero mmHg. The first or pre-fill step of the inflation phase has a duration T1 (e.g., about 1 second), during which the pressure increases to the pre-fill pressure P1 (e.g., about 8 mmHg). For example, a maximum pre-fill flow rate of between about 5 liters per minute (LPM) to 20 LPM may be used during the duration T1. The second or therapeutic step of the inflation phase has a duration T2 (e.g., 0.4 seconds), during which the pressure increases to the therapeutic pressure P2 (e.g., about 180 mmHg). For example, a minimum therapeutic flow rate between about 50 LPM and 90 LPM may be used during the duration T2. Gas is then vented from the inflatable chamber 26. The pressure profile is provided by way of example and not limitation. Other pre-fill pressures, times, and flow rates and other therapeutic pressures, times, and flow rates may be used without departing from the scope of the present invention. For example, the flow rates may be expressed in terms of variables, such as a maximum pre-fill flow rate of between about 5×LPM to 20×LPM, and a minimum therapeutic flow rate of between about 50×LPM and 90×LPM, in which "X" is an arbitrary constant.

The control system 42 may have various types of instructions for increasing the gas pressure in the inflatable chamber 26 during the inflation phase in accordance with the steps of the first inflation phase example outlined above. For example, the control system 42 may have time-based instructions. In other words, using the first step as an example, the storage medium 42B may have instructions for inflating the inflatable chamber 26 at a certain flow rate (e.g., 5-20 LPM) for an amount of time (no less than the predetermined pre-fill time) which has been predetermined to increase the gas pressure in the inflatable chamber 26 to no more than the predetermined pre-fill pressure. On the other hand, the control system 42 may have pressure-based instructions. In other words, using the first step again as an example, the storage medium 42B may have instructions for inflating the inflatable chamber 26 at a certain flow rate (e.g., 5-20 LPM) until the pressure in the inflatable chamber 26 reaches the predetermined pre-fill pressure (as monitored by the pressure sensor), where the flow rate is predetermined not to achieve the predetermined pre-fill pressure until at least the predetermined pre-fill time has expired. In summary, the storage medium 42B may have time-based and/or pressure-based instructions for increasing the pressure in the inflatable chamber 26 in accordance with the two steps of the first inflation phase example outlined above without departing from the scope of the present invention.

In one embodiment, the control system 42 may be programmed to execute pressure-based inflation control during the pre-fill step and to execute timing-based inflation control during the therapeutic step. For example, the storage medium 42B may have instructions to execute pressure-based inflation control during the pre-fill step by monitoring the pressure in the chamber during the pre-fill step and terminating the pre-fill step when a desired pressure is achieved. The relatively slow inflation during the pre-fill step enables relatively precise monitoring of the pressure and termination of the pre-fill step at about the desired pressure, not substantially above or below the desired pressure. The control system 42 may be programmed to then inflate the chamber 26 during the therapeutic step for a pre-determined inflation time determined by testing to achieve a desired end of therapeutic step pressure in the chamber. Timing-based control during the therapeutic step may be desirable because it may be difficult to end the therapeutic step precisely at the desired pressure based on sensed pressure due to the rapid increase of pressure during that step. Moreover, the control system 42 may measure the end of therapeutic step pressure to determine if the pre-determined therapeutic inflation time is successfully achieving the desired therapeutic pressure. If the measured therapeutic pressure is low, the target pressure for the end-of-pre-fill step may be increased for a subsequent inflation phase. If the measured therapeutic pressure is high, the target pressure for the end-of-pre-fill step may be decreased for a subsequent inflation phase. Accordingly, the end of pre-fill step pressure may be controlled to more accurately achieve the desired end-of-therapeutic step pressure when a timing based control of therapeutic step inflation is used.

In a second inflation phase example, to manage inflation of the inflatable chamber 26 to generate less noise as described above, the storage medium 42B may include instructions for increasing the gas pressure in the inflatable chamber 26 during the inflation phase in accordance with the following steps: (1) in a first step, increasing the gas pressure in the inflatable chamber 26 to no more than about a predetermined pre-fill pressure by delivering gas from the source of pressurized gas to the inflatable chamber 26 at a maximum pre-fill flow rate of no more than about a predetermined pre-fill flow rate; and (2) in a second step after the first step, increasing the gas pressure in the inflatable chamber 26 to at least a predetermined therapeutic pressure by delivering gas from the source of pressurized gas to the inflatable chamber 26 at a minimum flow rate of at least about a predetermined therapeutic flow-rate. In the first step, the predetermined pre-fill pressure may in one embodiment range from about 2 mmHg to 20 mmHg, and more desirably from about 5 mmHg to 12 mmHg. In the first step, the predetermined pre-fill flow rate may in one embodiment range from about 3 LPM to 22 LPM (3×LPM to 22×LPM), and more desirably about 5 to 15 LPM (5×LMP to 15×LPM). In the second step, the predetermined therapeutic pressure may in one embodiment range from about 120 mmHg to about 210 mmHg, and more desirably from about 160 mmHg to 200 mmHg. In the second step, the predetermined therapeutic flow rate may in one embodiment range from about 45 LPM to about 100 LPM (45×LPM to 100× LPM), more desirably 50 LPM to 90 LPM (50×LPM to 90×LPM), and more desirably 55 LPM to 80 LPM (55×LPM to 80×LPM).

The control system 42 may have various types of instructions for increasing the gas pressure in the inflatable chamber 26 during the inflation phase in accordance with the steps of the second inflation phase example outlined above. For example, the control system 42 may have time-based instructions. In other words, using the first step as an example, the storage medium 42B may have instructions for inflating the inflatable chamber 26 at a certain flow rate (e.g., 5-20 LPM) for an amount of time which has been predetermined to increase the gas pressure in the inflatable chamber 26 to no more than the predetermined pre-fill pressure. On the other hand, the control system 42 may have pressure-based instructions. In other words, using the first step again as an example, the storage medium 42B may have instructions for inflating the inflatable chamber 26 at a certain flow rate (e.g., 5-20 LPM) until the pressure in the inflatable chamber 26 reaches the predetermined pre-fill pressure (as monitored by the pressure sensor 42C), where the flow rate is predetermined not to achieve the predetermined pre-fill pressure until at least a desired pre-fill time has expired. In summary, the storage medium 42 may have time-based and/or pressure-based instructions for increasing the pressure in the inflatable chamber 26 in accordance with the two steps of the second inflation phase example outlined above without departing from the scope of the present invention. As explained above, the control system 42 may be programmed to execute pressure-based inflation control during the pre-fill step and to execute timing-based inflation control during the therapeutic step, whereby the pressure-based control during the pre-fill step may enable more precise achievement of the desired end of therapeutic phase pressure. It is understood constant or variable flow rates may be used according to the first and second steps above, as long as the flow rates do not exceed the maximum pre-fill flow rate in the first step or fall below the minimum therapeutic flow rate in the second step.

The control system 42 may be programmed for (e.g., the storage media 42B may have instructions for) executing the first steps (the pre-fill steps) of the first and second inflation phase examples outlined above for the inflation phase of every compression cycle or for the inflation phase of selected compression cycles only. For example, the pre-fill steps may only be used when relatively high flow requirements exist. It is understood high flow requirements normally exist in order to achieve desired therapeutic pressure in sufficiently low time to move blood. However, some inflation phases may require higher flow requirements relative to other inflation phases. The control system 42 may be programmed to normally not execute a pre-fill step during the inflation phase and to execute the pre-fill step only when relatively high flow requirements exist. The pressure sensor 42C and the physical characteristic sensors 42D, 42E may be adapted to indicate when relatively high flow requirements exist. The control system 42 may have instructions to execute the first and second steps in response to signals received from the pressure sensor 42C and physical characteristic sensors 42D, 42E representing the existence of relatively high flow requirements. For example, the pressure sensor 42C may indicate to the CPU 42A that the therapeutic pressure is not being achieved in appropriately short time (indicating a relatively high flow requirement), in which case the CPU 42A may begin executing a pre-fill step during the inflation phase for subsequent inflation phases. In another example, the first physical characteristic sensor 42D may indicate a compression garment 14 connected to the controller 12 has a relatively large inflatable chamber 26 or has multiple inflatable chambers 26, which may require relatively high flow for providing a greater volume of gas for achieving peak pressure, in which case the CPU 42A may begin executing a pre-fill step during the inflation phase. The pre-fill steps may be used in other circumstances in which relatively high flow requirements exist. For example, the control system 42 may be set for applying a relatively high therapeutic pressure, for example higher than normal therapeutic pressure, such that relatively high flow requirements exist, in which case the controller 12 may use a pre-fill step.

As is now apparent, utilization of a pre-fill step such as those described above results in less overall impingement noise. The pre-fill step also provides other advantages. For example, the pre-fill step may permit use of a pressurizer 40A having lower flow capacity which may be a smaller and/or lighter weight pressurizer. This is because a pre-fill step reduces the pressure differential in the inflatable chamber 26 which the source of pressurized gas 40 needs to overcome at the therapeutic flow rate. The pre-fill step may also increase the lifespan of the pressurizer 40A. For example, if a pressurizer 40A having a brush-type motor is used, using a pre-fill step helps to lower arcing that occurs at the brushes. When the pressurizer 40A is first turned on, the current typically spikes and then settles at a lower level. Using a pre-fill step helps to lower the arcing and thus reduces brush wear. Moreover, using a pre-fill step can decrease noise created by the pressurizer motor at the beginning of inflation. Many conventional systems apply the voltage required for therapeutic inflation immediately, which can be jarring because of sudden noise of the pressurizer turning on at high effective voltage. In the pre-fill step of the present disclosure, the pressurizer 40A turns on at a lower effective voltage. The pre-fill step may also lower power consumed by the pressurizer 40A per compression cycle.

In use, the foot cuff 14 is fluidly connected to the controller 12 and placed on a foot F of a person. The controller 12 is then initiated to cyclically inflate and deflate the foot cuff 14 to apply cycles of compression, each of which may include an inflation phase which includes a pre-fill step, or some of which may include a pre-fill step.

Figure 10:
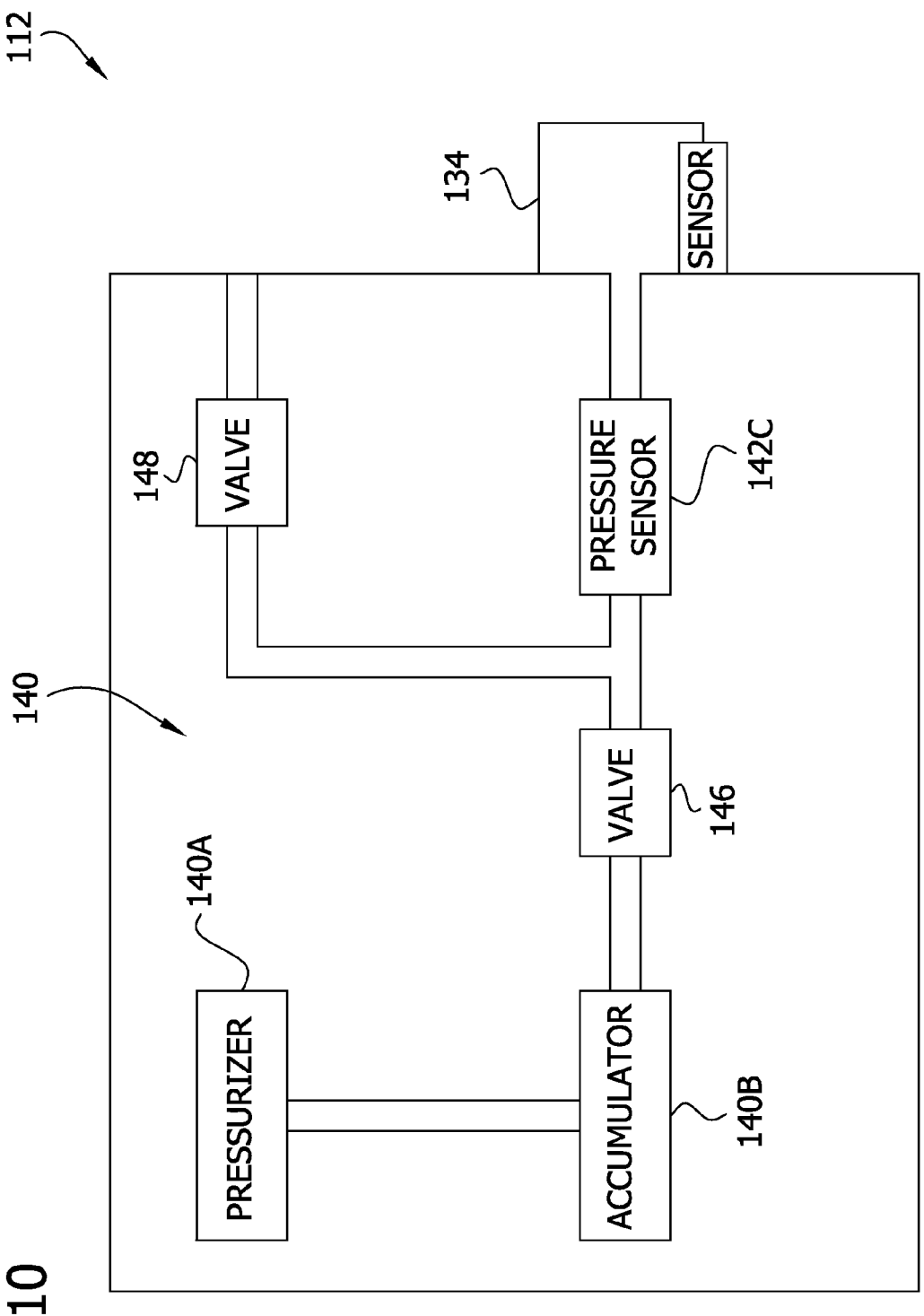
FIG. 10 is a schematic of another embodiment of a controller of the present invention.

FIG. 10 illustrates another exemplary embodiment of a controller 112 according to the present invention. The controller is similar to the controller 12 described above, and corresponding parts are indicated by corresponding reference numbers, plus 100. In this embodiment, the controller 112 has a source of pressurized gas 140 which includes a pressurizer 140A, an accumulator 140B, an inflation valve 146, an exhaust valve 148, and a connector 134. The controller also includes a pressure sensor 142C. This embodiment of the controller 112 is capable of managing flow of gas into the inflatable chamber 26 as described above. In this embodiment, instead of having inflation valves in parallel (e.g. valves 46A, 46B), the controller 112 has a variable flow valve 146. For example, the valve 146 may have two open positions. When in the first open position, the valve 146 may permit flow at the pre-fill flow rate, and, when in the second open position, the valve 146 may permit flow at the therapeutic flow rate. Thus, controller 112 may be programmed to move the valve 146 to the first open position to deliver gas to the inflatable chamber 26 at the pre-fill flow rate (during the first step) and move the valve 146 to the second open position to deliver gas to the inflatable chamber 26 at the therapeutic flow rate (during the second step). The accumulator 140B may be omitted without departing from the scope of the present invention.

Figure 11:
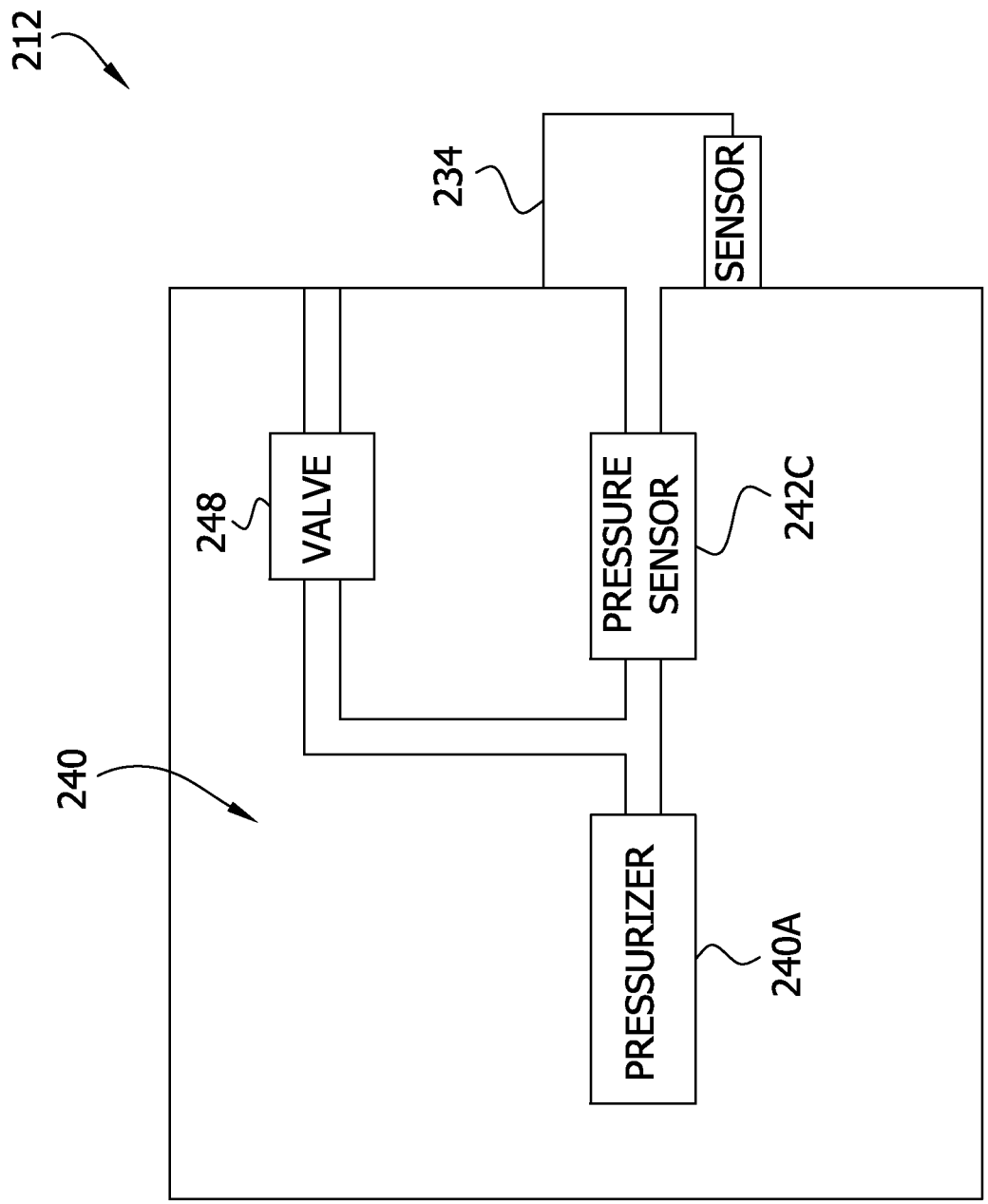
FIG. 11 is a schematic of another embodiment of a controller of the present invention.

FIG. 11 illustrates another exemplary embodiment of a controller 212 according to the present invention. The controller is similar to the controller 12 described above, and corresponding parts are indicated by corresponding reference numbers, plus 200. In this embodiment, the controller 212 has a source of pressurized gas 240 which includes a pressurizer 240A, an exhaust valve 248, and a connector 234. The controller also includes a pressure sensor 242C. This embodiment of the controller 212 is capable of managing flow of gas into the inflatable chamber 26 as described above. In this embodiment, instead of having an inflation valve (e.g., valve 46A or 46B), the controller 212 has a pressurizer 240A in the form of a variable speed pump. For example, the pressurizer 240A may have at least two speeds. At the first speed, the pressurizer 240A may deliver gas flow at the pre-fill flow rate, and, at the second speed, the pressurizer 240A may deliver gas flow at the therapeutic flow rate. Thus, controller 212 may be programmed to operate the pressurizer 240A at the first speed to deliver gas to the inflatable chamber 26 at the pre-fill flow rate (during the first step) and operate the pressurizer 240A at the second speed to deliver gas to the inflatable chamber 26 at the therapeutic flow rate (during the second step).

Figure 12:
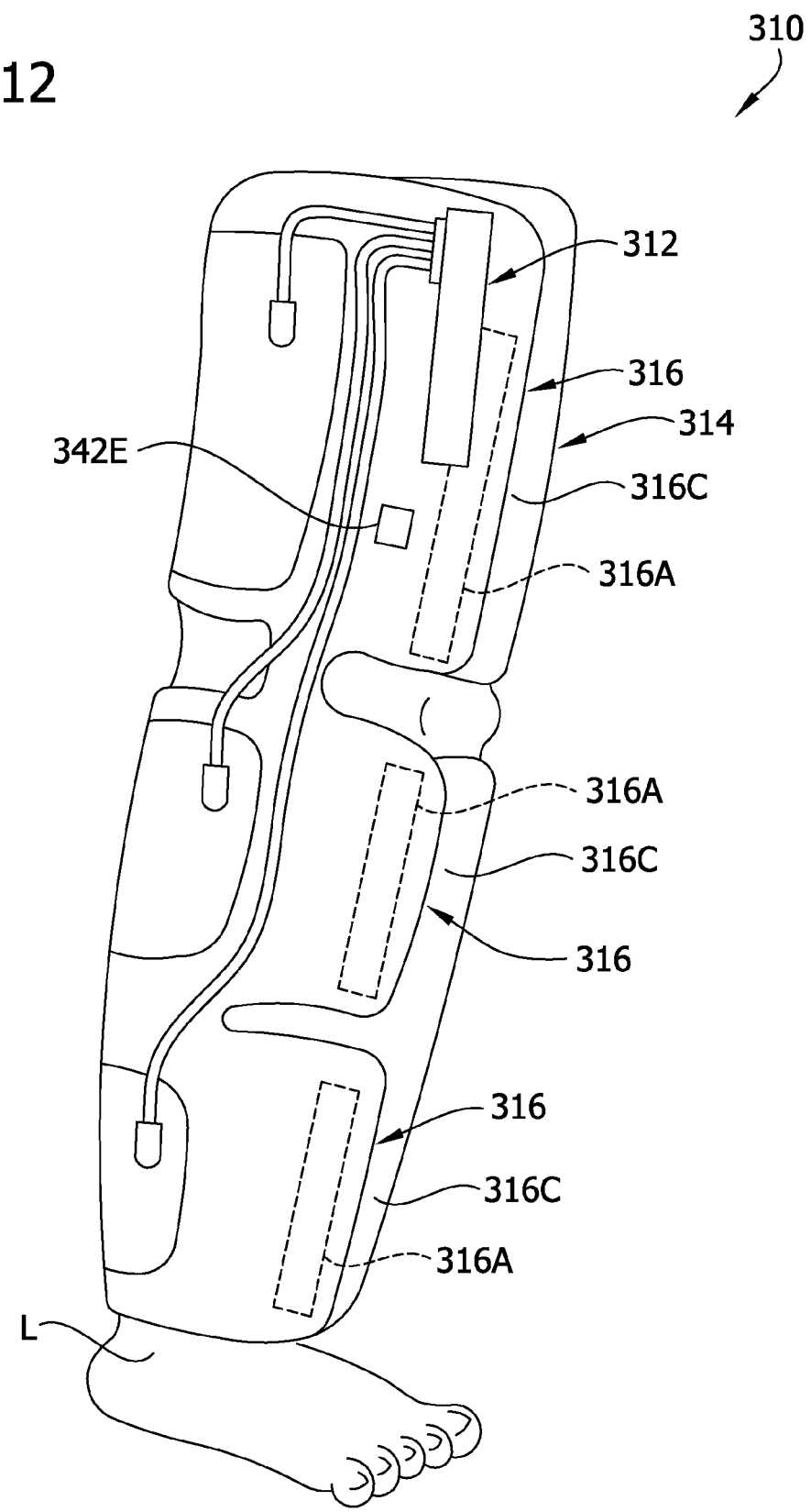
FIG. 12 is a perspective of another embodiment of a compression system of the present invention as applied to a leg, the compression system including a compression garment and a controller.

FIG. 12 illustrates a second embodiment of a compression system 310 according to the present invention. The compression system is similar to the compression system 10 described above, and similar parts are designated by corresponding reference numbers, plus 300. In this embodiment, the compression garment is a limb sleeve 314. The controller 312 may be mounted or supported on the limb sleeve 314 such that it is portable or readily movable with the limb sleeve when worn.

As will be described, this embodiment of the compression system 310 includes similar aspects of inflation gas flow management as the first embodiment of the compression system 10 in addition to other aspects of inflation gas flow management. The inflation gas flow management associated with this embodiment results in less overall impingement noise, as with the embodiment described above. However, a particular advantage of note with respect to the controller 312 of this embodiment is that the inflation gas flow management may permit use of a pressurizer 340A having lower flow capacity which may be a smaller and/or lighter weight pressurizer. This is because the pre-fill step reduces the pressure differential in the inflatable chambers of the limb sleeve 314 which the source of pressurized gas 340 needs to overcome at the therapeutic flow rate. Accordingly, the controller 312 may be made more portable and easier to mount or support on the limb sleeve 314.

The illustrated limb sleeve is a leg sleeve 314 configured to be applied to a leg L and has a "thigh length" size, meaning the leg sleeve extends generally from the ankle to the thigh. Other sizes and shapes of leg sleeves (e.g., "knee length" extending generally from the ankle to the knee) and leg sleeves adapted for covering additional body parts (e.g., the leg and the foot) may be used without departing from the scope of the present invention.

Figure 13:
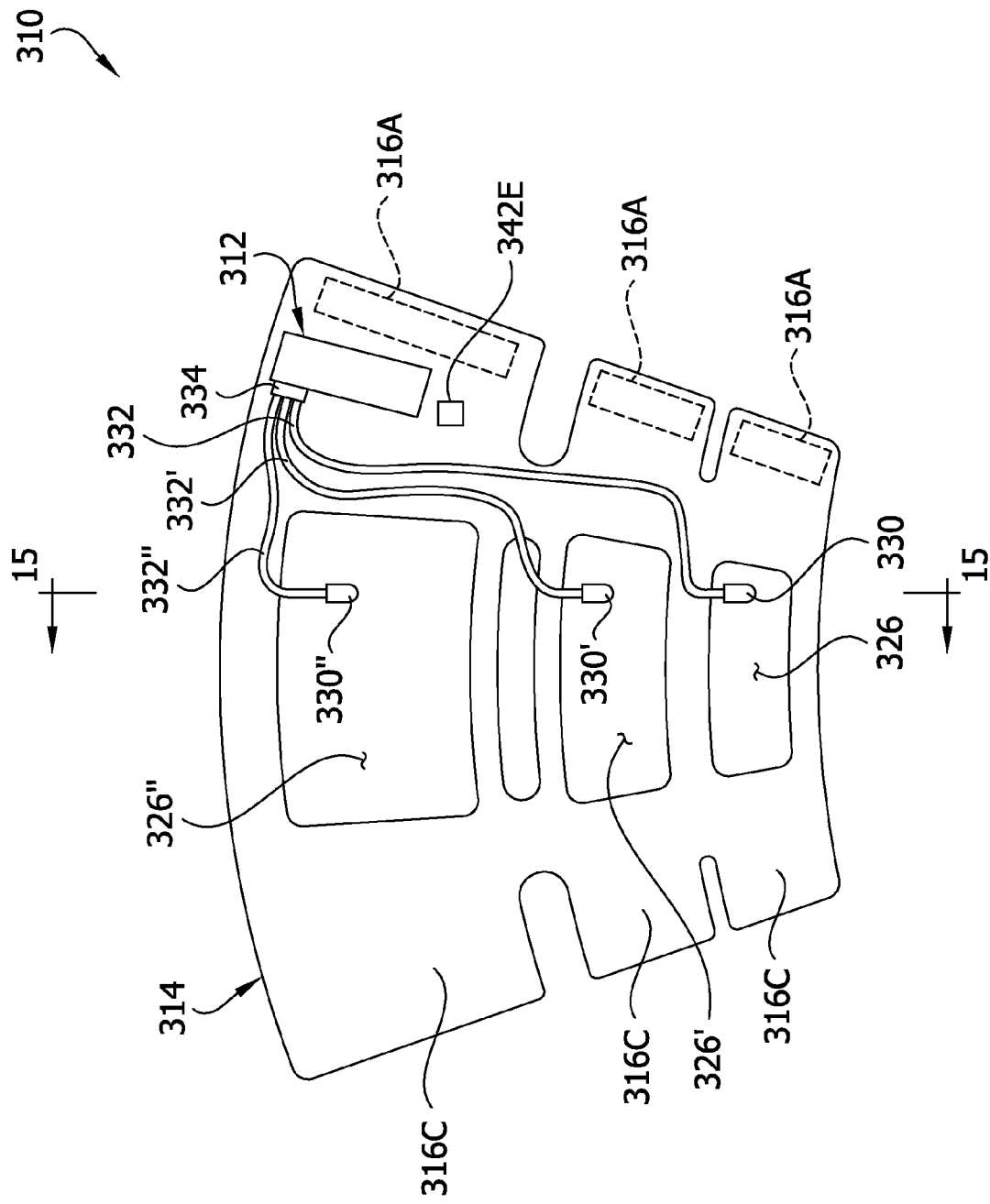
FIG. 13 is a rear elevation of the compression garment.
Figure 14:
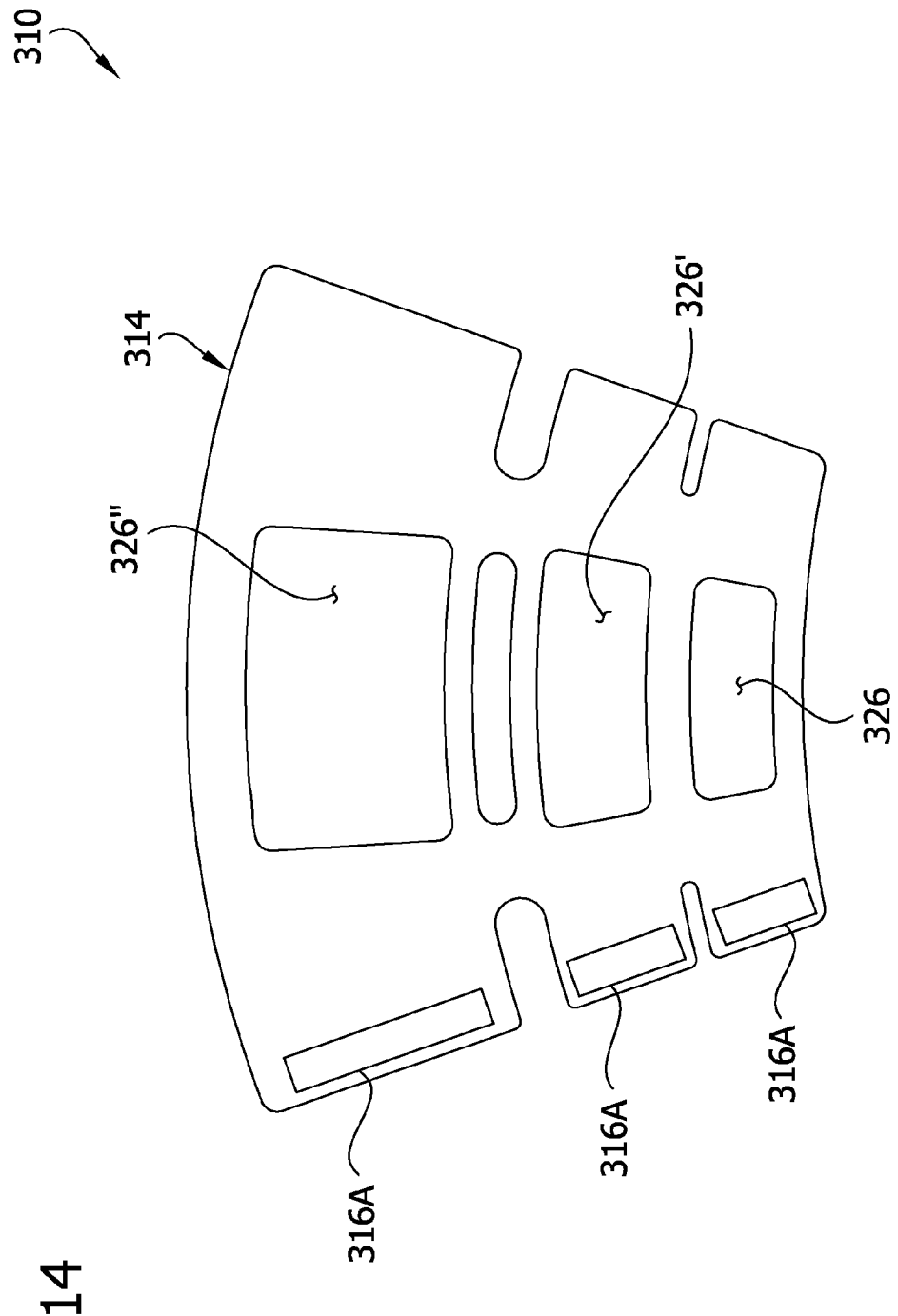
FIG. 14 is a front elevation of the compression garment.

FIGS. 13 and 14 illustrate the leg sleeve 314 in an open, unwrapped configuration. To position the leg sleeve 314 on a leg L, a central portion of the sleeve is applied to the rear of the leg and opposite sides of the sleeve are wrapped around the leg into overlapping relationship. Releasable fastening assemblies 316 are provided for securing the leg sleeve 314 on the leg L in a self-retaining position in which it is wrapped around the leg. In the illustrated embodiment, the fastener assemblies 316 include sections of hook fabric 316A adapted for releasably fastening to loop fabric 316C. Limb sleeves having other configurations may be used without departing from the scope of the present invention. For example, other fastening assemblies may be used, and the limb sleeve 314 may have a tubular construction such that it is positioned on the limb by sliding it over the limb.

Figure 15:
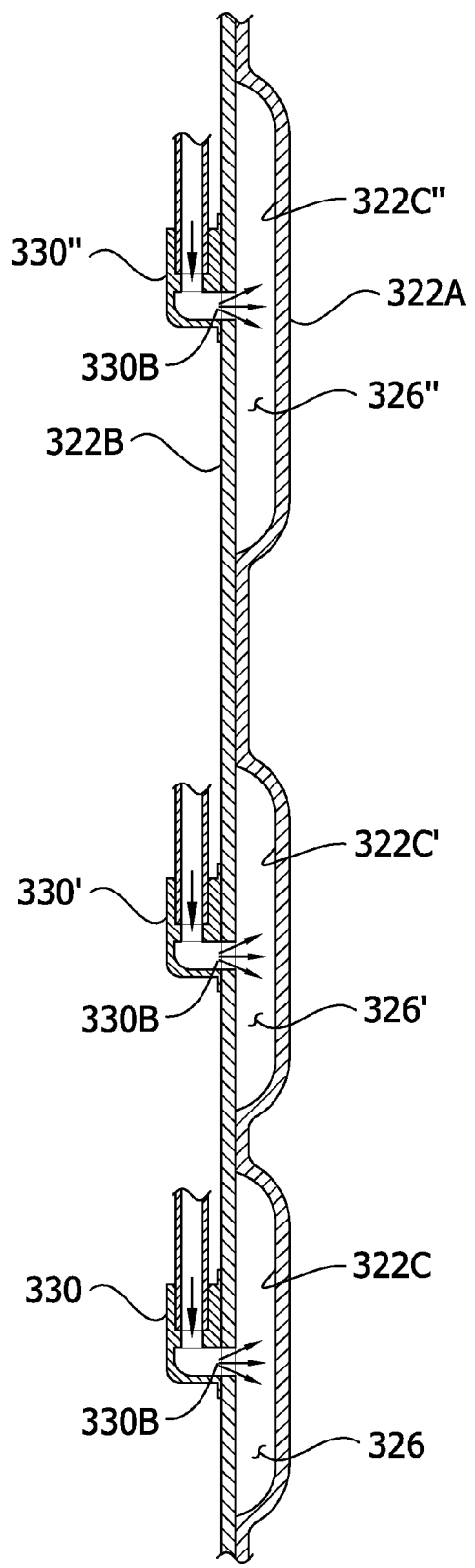
FIG. 15 is an enlarged section of the compression garment taken in the plane including line 15-15 in FIG. 13.

As shown in FIGS. 13-15, the leg sleeve 314 includes three inflatable chambers 326, 326', 326". For example, in use, the first inflatable chamber 326 may overlie the ankle, the second inflatable chamber 326' may overlie the calf, and the third inflatable chamber 326" may overlie the thigh. As known by persons having ordinary skill in the art, the three inflatable chambers 326, 326', 326" may be inflated intermittently and sequentially (e.g., from ankle to thigh) or in other manners for enhancing flow of blood. The leg sleeve 314 includes inner and outer layers 322A, 322B positioned in face-to-face opposing relationship between which the inflatable chambers 326, 326', 326" are formed. The inner and outer layers 322A, 322B may be sealed together using suitable methods about boundary lines which define the three inflatable chambers 326, 326', 326". For example, the inner and outer layers 322A, 322B may be sealed together using RF welding, heat sealing, or adhesives. Other types of mechanical and/or chemical processes may be used to join the layers 322A, 322B. Similar techniques may be used to join the layers 322A, 322B at other locations, such as around the perimeters of the layers. The inner and outer layers 322A, 322B may comprise any suitable gas-impermeable material, such as a pliable PVC or a laminate including a pliable PVC layer. Optionally, inner and outer cover layers (not shown) may be provided. Limb sleeves having other numbers of inflatable chambers, inflatable chambers having other sizes or shapes, or other configurations of layers may be used without departing from the scope of the present invention.

Referring again to FIG. 13, the controller 312 is connected in fluid communication with each of the three inflatable chambers 326, 326', 326" via conduits 332, 332', 332" extending from the inflatable chambers. The conduits 332, 332', 332" are connected in fluid communication with the inflatable chambers 326, 326', 326" via ports 330, 330', 330", which may have constructions similar to the port 30 described above. Opposite ends of the conduits 332, 332', 332" are connected to a common connector 334, which is adapted for connecting the conduits in fluid communication with the controller 312 so that gas can be delivered from the controller to the inflatable chambers 326, 326', 326" individually.

Figure 16:
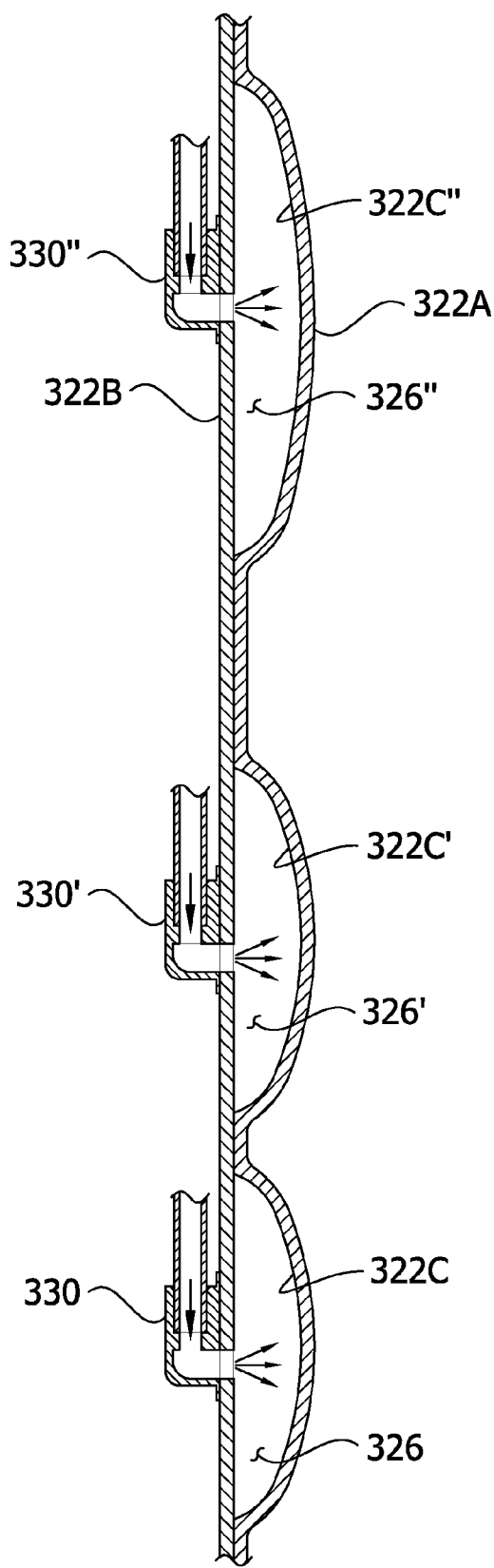
FIG. 16 is a view similar to FIG. 15 but showing the compression garment in a partially inflated configuration.
Figure 17:
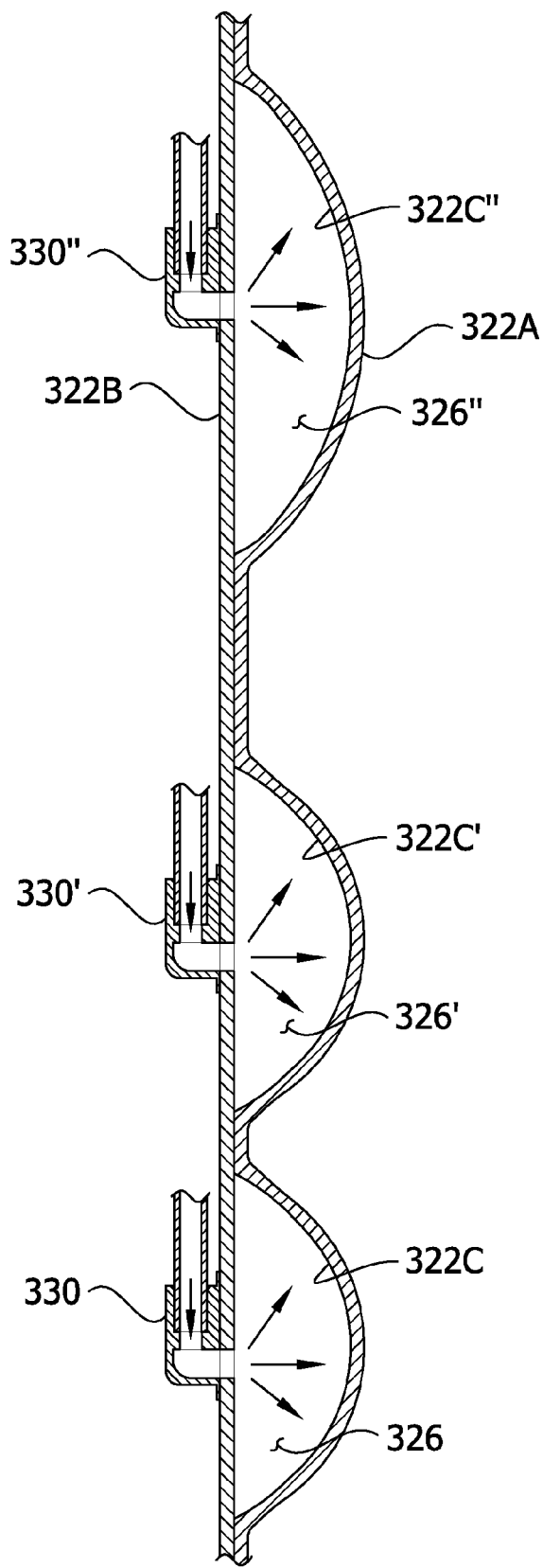
FIG. 17 is a view similar to FIG. 15 but showing the compression garment in a fully inflated configuration.

As shown in FIG. 15, each inflatable chamber 326, 326', 326" includes a gas impingement surface 322C, 322C', 322C" opposite the respective port second opening 330B, 330B', 330B". When the inflatable chambers 326, 326', 326" are inflated, gas delivered into the inflatable chambers enters the chambers in the form of a gas jet which impinges against the impingement surfaces 322C, 322C', 322C". FIGS. 15-17 illustrate the inflatable chambers 326, 326', 326" in generally deflated, partially inflated, and fully inflated configurations, respectively. It is understood the configurations may appear other than shown when the sleeve 314 is wrapped on a leg L in use.

Figure 18:
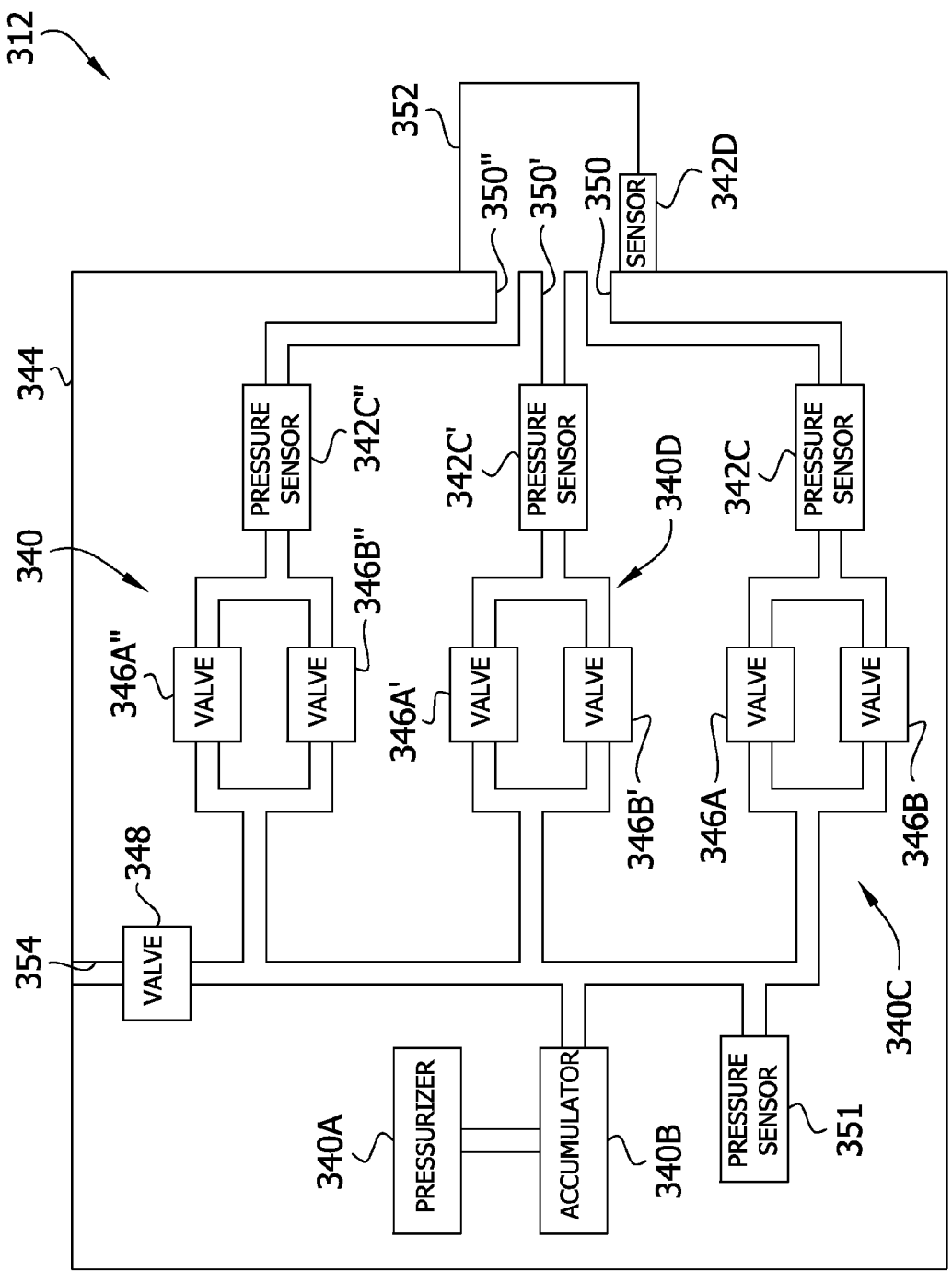
FIG. 18 is a schematic of the controller of FIG. 12.
Figure 19:
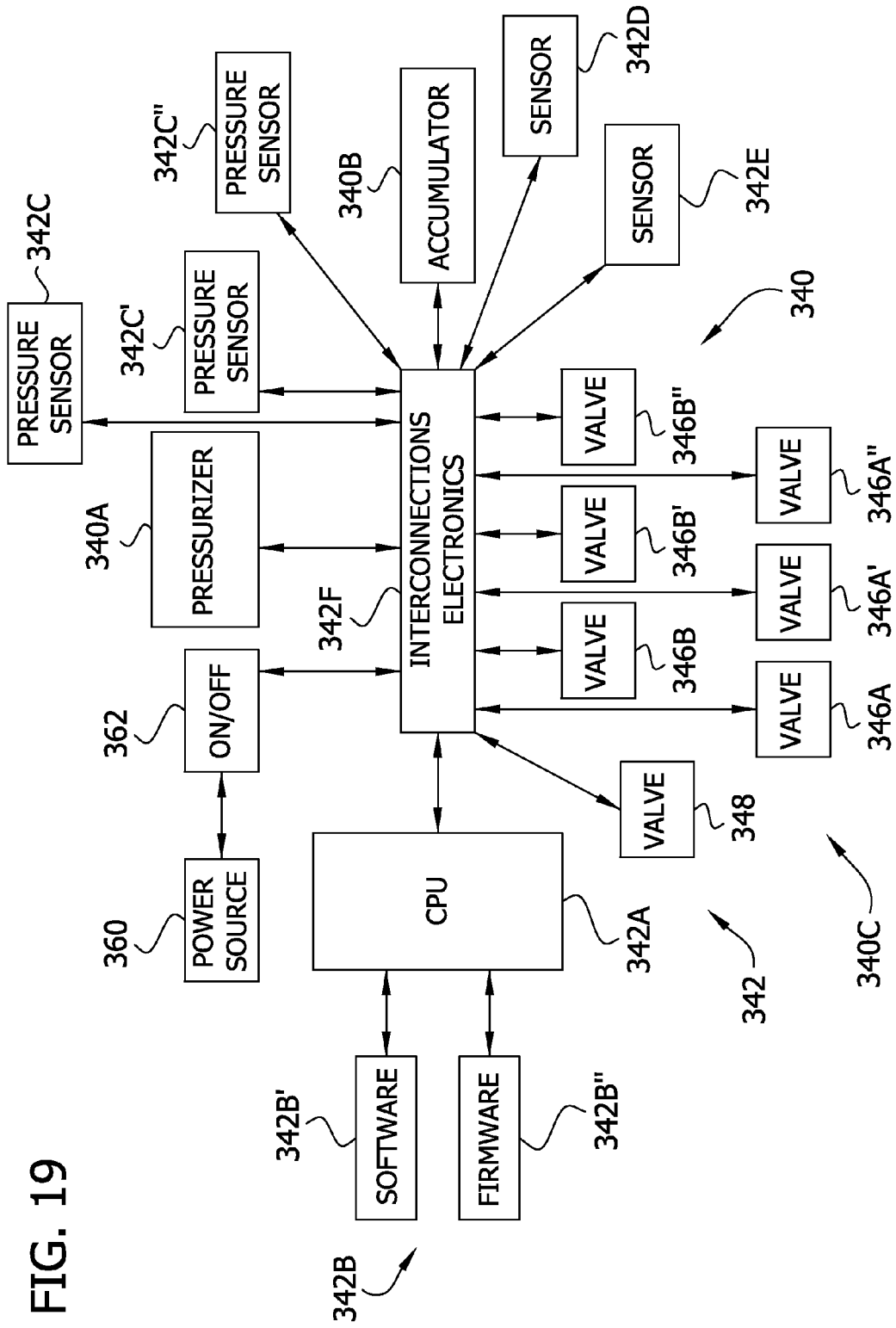
FIG. 19 is a schematic of a control system of the controller.

An exemplary embodiment of a controller 312 for use with the leg sleeve 314 is illustrated schematically in FIGS. 18 and 19. In general, the controller 312 includes a source of pressurized gas, generally indicated by 340, and a control system, generally indicated by 342 (FIG. 19), for controlling delivery of gas to and from the inflatable chambers 326, 326', 326" of the leg sleeve 314. The source of pressurized gas 340 and the control system 342 may be housed together in a housing 344. As shown schematically in FIG. 18, the source of pressurized gas 340 includes a pressurizer 340A, an accumulator 340B, valving 340C, and gas flow passaging 340D connecting respective components in fluid communication with each other. The valving 340C includes three pairs of first inflation valves 346A, 346A', 346A" and second inflation valves 346B, 346B', 346B" positioned in parallel along the gas flow passaging 340D and an exhaust valve 348. Pressure sensors 342C, 342C', 342C" are provided downstream of the valving 340C. Alternatively or in addition, a pressure sensor 351 may be provided in the common manifold downstream from the accumulator and upstream from the valving 340C. The gas flow passaging 340D includes three ports 350, 350', 350" for delivering gas to and receiving gas from respective inflatable chambers 326, 326', 326". A connector 352 is provided at the ports 350, 350', 350" for operatively connecting the controller 312 in fluid communication with the leg sleeve 314 via the leg sleeve connector 334. The gas flow passaging 340D also includes an exhaust 354 downstream from the exhaust valve 348 for exhausting or venting gas from the inflatable chambers 326, 326', 326".

In use, the pressurizer 340A generates pressurized gas which is stored in the accumulator 340B and selectively delivered to the inflatable chambers 326, 326', 326" through respective pairs of first and second inflation valves 346A, 346B, 346A', 346B', 346A", 346B". Each inflation valve has a closed position in which it prevents gas flow through the valve and an open position in which it permits gas to flow through the valve. The first valves 346A, 346A', 346A" have smaller flow areas (e.g., a smaller orifices) than the second valves 346B, 346W, 346B". Thus, when the first and second valves of each pair are in their respective open positions, the first valve 346A, 346A', 346A" permits gas flow at a lower rate than the second valve 346B, 346B', 346B". Gas is selectively vented from the inflatable chambers 326, 326', 326" via the exhaust valve 348 out of the exhaust 354.

Sources of pressurized gas configured other than illustrated or described herein, such as similar to those described above, may be used without departing from the scope of the present invention. For example, the accumulator 340B may be omitted, other valving arrangements may be used, and other configurations of flow passaging may be used. In another example, the pressurizer 340A may be omitted in favor of a source of compressed gas.

As shown schematically in FIG. 19, the control system 342 may include a central processing unit (CPU) 342A, a tangible storage medium 342B, pressure sensors 342C, 342C', 342C", and two physical characteristic sensors 342D, 342E. The control system 342 is similar to the control system 42 described above but includes connections to additional components (e.g., valves 346A', 346B', 346A", 346B") corresponding to the parts of the controller 312 associated with the additional inflatable chambers 326', 326". The control system 342 is selectively energized by a power source 360 (e.g., a battery or utility power) by actuating an ON/OFF switch 362. The control system also includes interconnections electronics 342F which operatively connect the other components of the control system and operatively connect the control system to the source of pressurized gas 340. The CPU 342A may be a microprocessor or the like. The tangible storage medium 342B may include forms of storage such as software 342B' and firmware 342B". The CPU 342A is adapted for reading and executing instructions stored in the storage medium 342B. The CPU 342A provides control signals via the interconnection electronics 342F to operate the source of pressurized gas 340. More specifically, the CPU 342A may provide control signals for operating the pressurizer 340A, the accumulator 340B, and/or the valving 340C to manage inflation and deflation of the inflatable chambers 326, 326', 326". For example, the interconnection electronics 342F transmit signals from the CPU 342A to the pressurizer 340A, accumulator 340B, and/or valving 340C wirelessly or via electrical or fiber optic lines. The pressure sensors 342C, 342C', 342C" and physical characteristic sensors 342D, 342E may communicate with the CPU 342A, for example, wirelessly or via electrical or fiber optic lines. The pressure sensors 342C, 342C', 342C" sense gas pressure in the flow passaging 340D indicative of the gas pressure in the respective inflatable chambers 326, 326', 326" and generate signals which are communicated to the CPU 342A indicative of the sensed pressures.

The physical characteristic sensors may include a first sensor 342D adapted for sensing a type of compression garment connected to the controller and a second sensor 342E which is adapted for sensing a physical characteristic of the leg sleeve 314 and/or the leg L. For example, the first sensor 342D may be provided on the controller connector 352 for sensing the type of leg sleeve 314 (e.g., number and/or volume of inflatable chambers 326, 326', 326") as indicated by an indicator 334A provided on the connector 334 of the leg sleeve 314. Thus, this sensor 342D may indicate to the CPU 342A flow requirements for inflating the leg sleeve 314. The second sensor 342E may be provided in the form of an accelerometer or other suitable sensor (FIGS. 12 and 13) on the leg sleeve 314 for sensing physical characteristics such as orientation or movement of the leg sleeve 314 or leg L. Alternatively, the sensor 342E may be provided on the controller 312. The second sensor 342E may indicate physical characteristics which increase the flow requirements to inflate the leg sleeve 314 sufficiently to achieve efficacious compression therapy. Control systems having other configurations may be used without departing from the scope of the present invention.

As with the control system 42 described above, the control system 342 is programmed for executing successive compression cycles to impart intermittent compression therapy. Each compression cycle includes an inflation phase during which the control system 342 directs pressurized gas from the source of pressurized gas 340 to the inflatable chambers 326, 326', 326" to increase gas pressure in the inflatable chambers to a desired "peak" pressure to compress the leg L. Each compression cycle also includes a vent phase after the inflation phase during which the control system 342 permits gas to vent from the inflatable chambers 326, 326', 326" to decrease gas pressure in the inflatable chambers to relieve compression on the leg L. The compression cycles are executed one after another for a selected duration for imparting intermittent compression therapy to the leg L. The controller 312 may inflate the chambers 326, 326', 326" to different pressures and inflate the chambers sequentially (e.g., from ankle to thigh) to impart gradient, sequential compression therapy to the leg L.

The controller 312 may be programmed to manage flow of gas into the inflatable chambers 326, 326', 326" to permit use of a smaller and/or lighter weight pressurizer 340A in the form of a pump and to reduce the amount of noise generated during inflation of the inflatable chambers 326, 326', 326". In general, the controller 312 may be programmed for (i.e., the storage medium 342B has instructions for) inflating any one or two of the inflatable chambers 326, 326', 326", or all three of the inflatable chambers, at a first reduced flow rate or "pre-fill" flow rate before completing inflation of the inflatable chambers at a second rapid flow rate or "therapeutic" flow rate. For simplicity, such two-step inflation will be described with respect to the ankle chamber 326. The controller 312 begins inflation of the inflatable chamber 326 by increasing the gas pressure in the inflatable chamber at the pre-fill flow rate. In the embodiment illustrated in FIG. 18, the control system 342 may open the first inflation valve 346A (when the second inflation valve 346B is closed) to deliver gas to the inflatable chamber 326 through the first inflation valve at the pre-fill flow rate. In other words, the first inflation valve 346A may be configured for example, with an appropriately sized orifice, or the flow output from the source of pressurized gas 340 may be electronically controlled, to permit flow at the pre-fill flow rate when open. The pre-fill flow rate is less than the conventional rapid flow rate. The controller 312 completes inflation of the inflatable chamber 326 by increasing the gas pressure in the inflatable chamber at the therapeutic flow rate, which is greater than the pre-fill flow rate and which achieves peak pressure in a sufficiently minimal time to impart efficacious compression therapy. In the embodiment illustrated in FIG. 18, the control system 342 may open the second inflation valve 346B (with or without the first inflation valve 346A closed) to deliver gas to the inflatable chamber 326 through the second inflation valve at the therapeutic flow rate. In other words, the second inflation valve 346B may be configured for example, with an appropriately sized orifice, or the flow output from the source of pressurized gas 340 may be electronically controlled, to permit flow at the therapeutic flow rate when open. Because the inflatable chamber 326 was partially inflated at the pre-fill flow rate, the pressurizer 340A has less pressure differential to overcome at the therapeutic flow rate to achieve the peak pressure in the inflatable chamber 326. Managing the inflation of the inflatable chambers 326, 326', 326" in this way permits use of a smaller and/or lighter weight pressurizer 340A. Moreover, as explained with respect to the compression system 10 of the first embodiment, less overall impingement noise is created. In particular, less impingement noise is generated at the beginning of the inflation phase at the pre-fill flow rate.

As mentioned above, the two-step inflation regimen may be executed with respect to the first, second, and third inflatable chambers 326, 326', 326" or any combination thereof. In other words, one, two, or all three of the inflatable chambers 326, 326', 326" may be inflated according to a similar two-step regimen (pre-fill and therapeutic steps) beginning at the same time or at different times to the same pressure or to different pre-fill pressures, as will become apparent. For example, the first valve 346A, 346A', 346A" of each pair may be adapted for permitting different pre-fill flow rates, and the second valves 346B, 346B', 346B" of each pair may be adapted for permitting different therapeutic flow rates.

To manage inflation of the inflatable chambers 326, 326', 326" as described above, the storage medium 342B may include appropriate instructions. In a first inflation phase example, the storage medium 342B may include instructions for increasing the gas pressure in at least one of the inflatable chambers 326, 326', 326" during the inflation phase in accordance with the following steps: (1) in a first step, increasing the gas pressure in the inflatable chamber 326, 326', 326" to no more than about a predetermined pre-fill pressure in no less than a predetermined pre-fill time; and (2) in a second step after the first step, increasing the gas pressure in the inflatable chamber 326, 326', 326" to at least about a predetermined therapeutic pressure in no more than a predetermined therapeutic time. In the first step, the predetermined pre-fill pressure may in one embodiment range from about 1 mmHg to 22 mmHg, and more desirably from about 2 mmHg to 10 mmHg. In the first step, the predetermined pre-fill time may in one embodiment range from about 1 seconds to 8 seconds, and more desirably from about 1.5 second to 5 seconds. In the second step, the predetermined therapeutic pressure may in one embodiment range from about 25 mmHg to about 75 mmHg, and more desirably from about 35 mmHg to 65 mmHg. In the second step, the predetermined therapeutic time may in one embodiment range from about 0.5 seconds to about 8 seconds, and more desirably from about 1 second to about 4 seconds.

Figure 20:
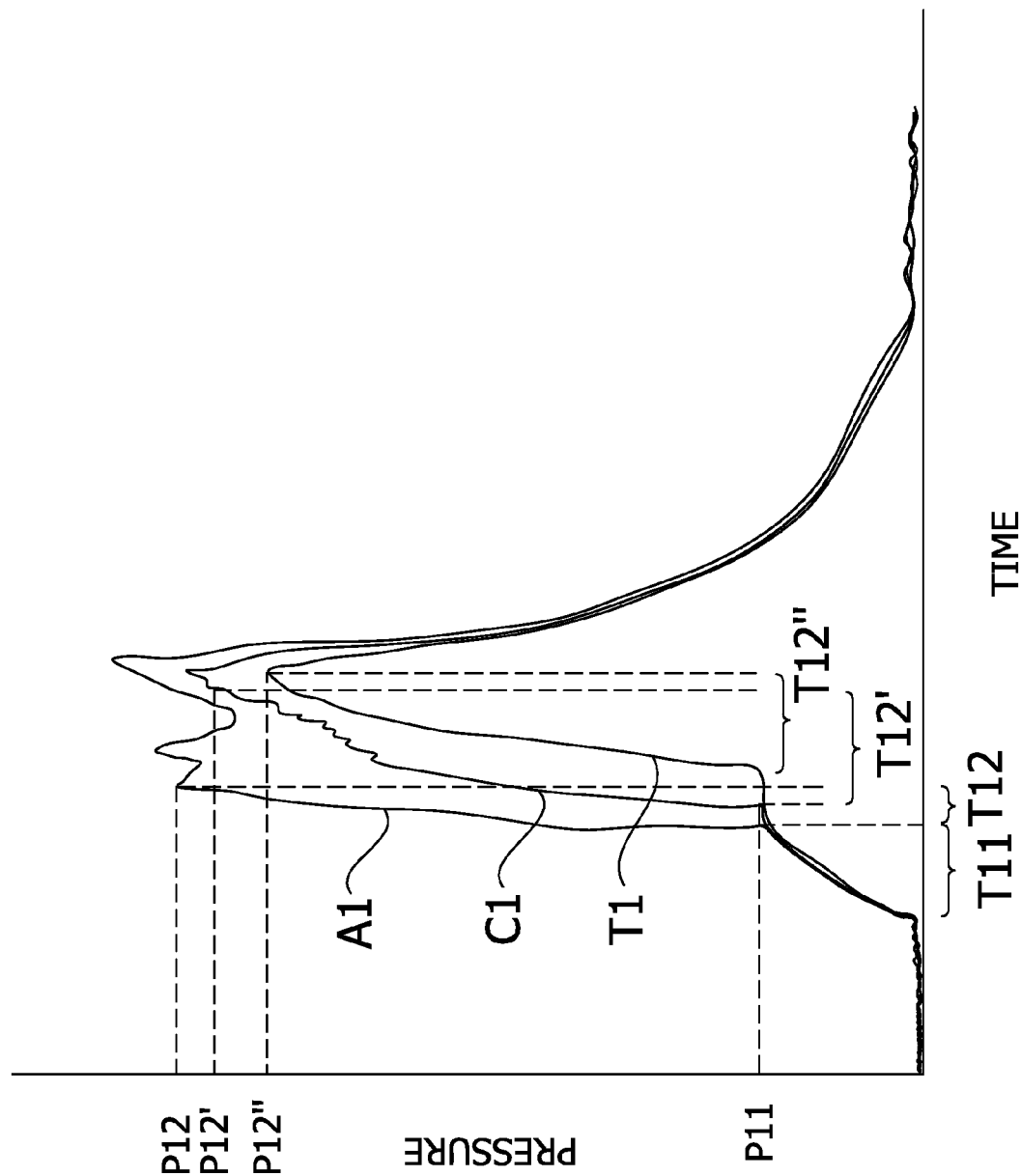
FIG. 20 is a graph showing an example of profiles of pressure in the compression garment according to the present invention.
Figure 21:
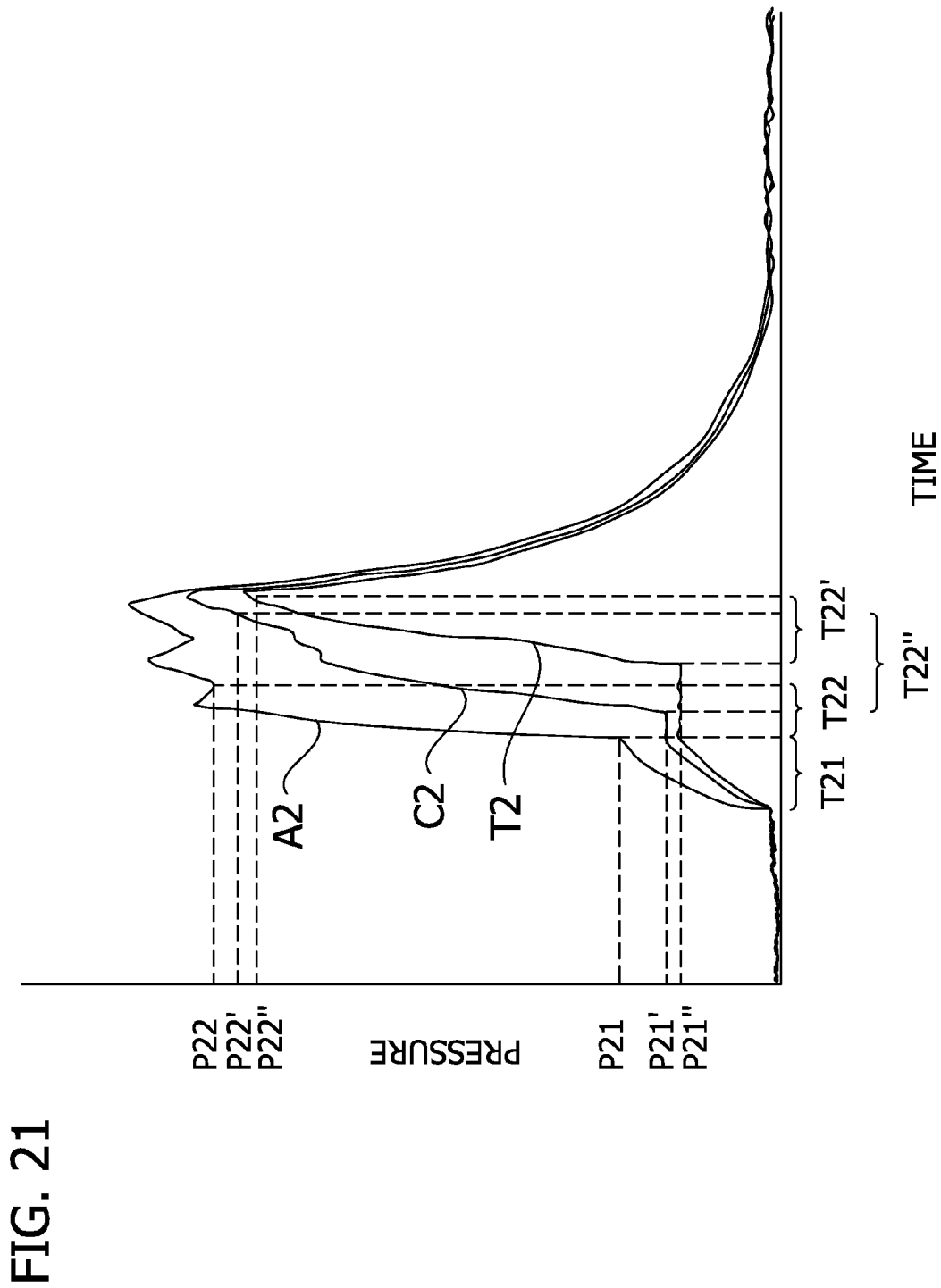
FIG. 21 is a graph showing another example of profiles of pressure in the compression garment according to the present invention.
Figure 22:
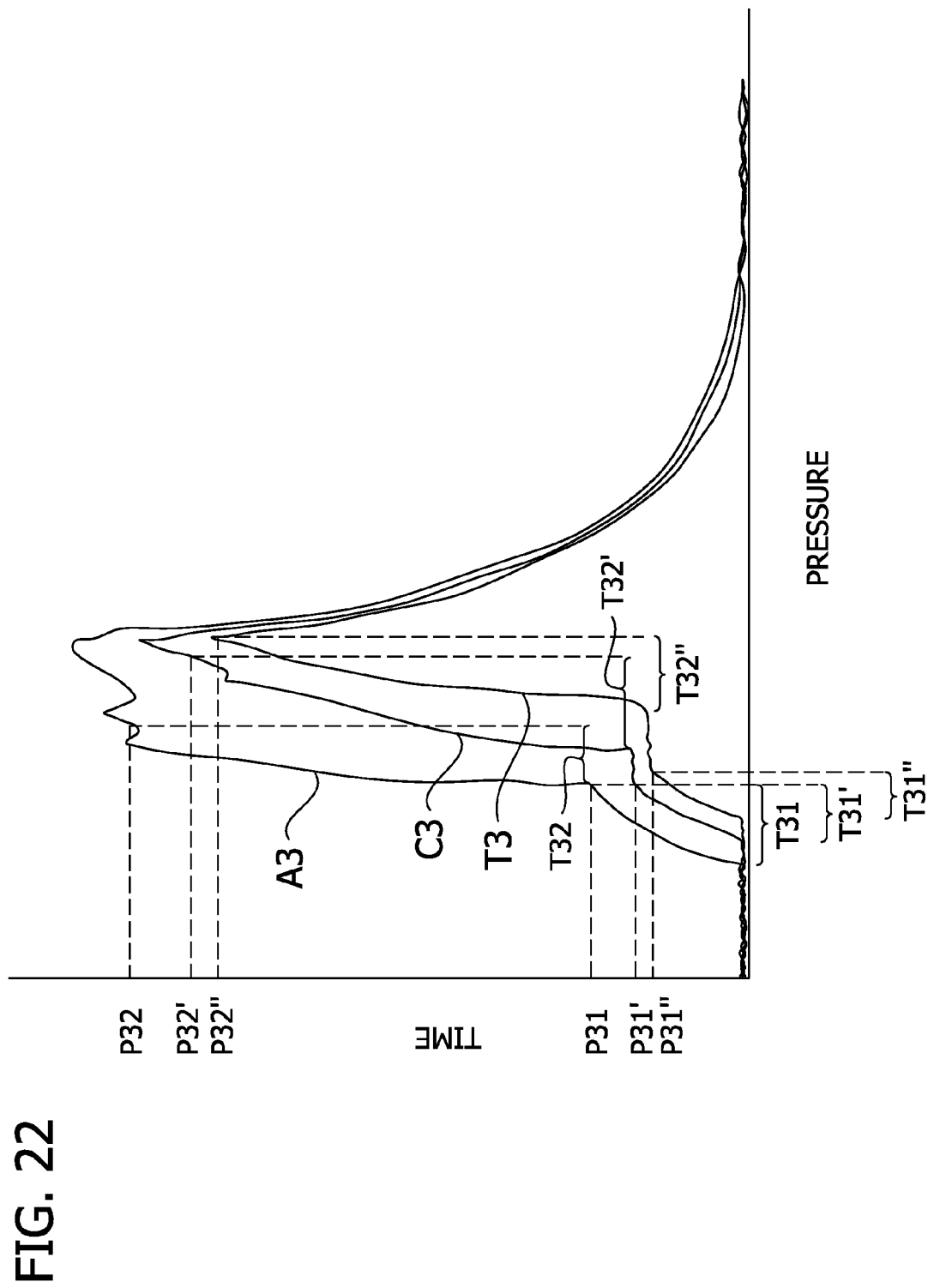
FIG. 22 is a graph showing another example of profiles of pressure in the compression garment according to the present invention.
Figure 23:
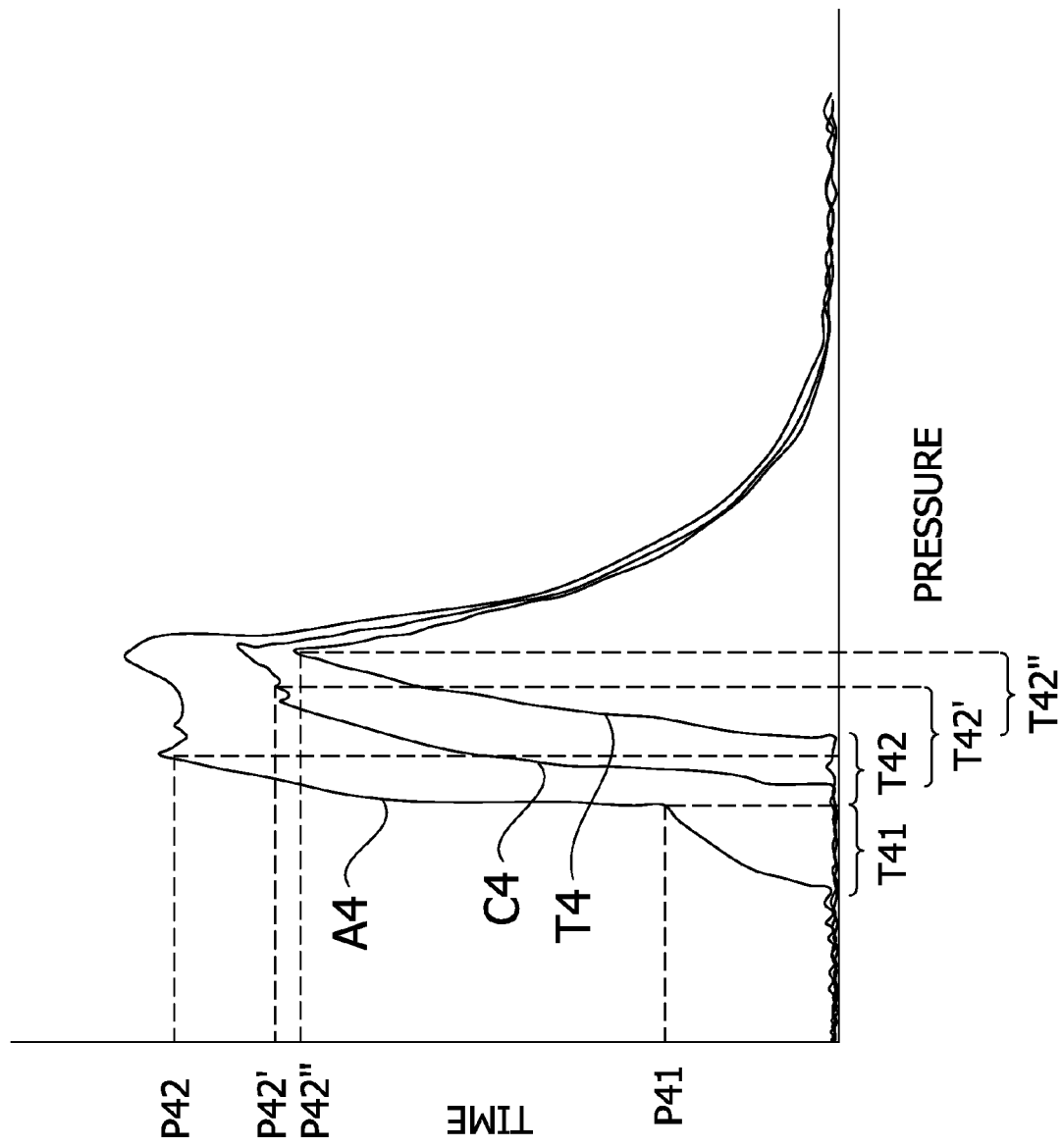
FIG. 23 is a graph showing another example of profiles of pressure in the compression garment according to the present invention.

FIGS. 20-23 illustrate graphs of profiles of pressure in the inflatable chambers 326, 326', 326" during different example compression cycles of the present invention. In general, FIGS. 20-22 illustrate graphs of pressure profiles in the inflatable chambers 326, 326', 326" where the inflation phase for each of the inflatable chambers includes a pre-fill step, and FIG. 23 illustrates a graph of a pressure profile in the inflatable chambers where only the inflation phase for the inflatable chamber 326 associated with the ankle includes a pre-fill step.

FIG. 20 illustrates a graph of a profile of pressures in the inflatable chambers 326, 326', 326" where the first or pre-fill step of the inflation phase for each inflatable chamber begins at about the same time, and where the chambers are inflated to about the same pre-fill pressure. The profiles of pressure in the ankle, calf, and thigh chambers 326, 326', 326" are represented by curves A1, C1, T1, respectively. The pre-fill steps of the inflation phases for each bladder have a duration T11 (e.g., about 3 seconds), during which the pressure increases in each of the inflatable chambers 326, 326', 326" to the pre-fill pressure P11 (e.g., about 6 mmHg). The second or therapeutic step of the inflation phases begin sequentially and have respective durations T12, T12', T12" (e.g., 2.7, 3, and 5.3 seconds), during which the pressure increases to the respective therapeutic pressures P12, P12', P12" (e.g., about 45, 40, and 30 mmHg).

FIG. 21 illustrates a graph of profiles of pressure in the inflatable chambers 326, 326', 326" where the pre-fill steps for the inflatable chambers begin at about the same time, and where during the pre-fill steps the inflatable chambers are inflated to different (gradient) pre-fill pressures. The profiles of pressure in the ankle, calf, and thigh chambers 326, 326', 326" are represented by curves A2, C2, T2, respectively. The pre-fill steps of the inflation phases for each bladder have a durations T21 (e.g., about 3 seconds), during which the pressure increases in each of the inflatable chambers 326, 326', 326" to the respective pre-fill pressures P21, P21', P21" (e.g., about 8, 6, and 4 mmHg). The ankle chamber 326 is inflated to a higher pre-fill pressure than the calf chamber 326', which is inflated to a higher pressure than the thigh chamber 326". The therapeutic step of the inflation phases begin sequentially and have respective durations T22, T22', T22" (e.g., 2.7, 3, and 5.3 seconds), during which the pressure increases to the respective therapeutic pressures P22, P22', P22" (e.g., about 45, 40, and 30 mmHg).

FIG. 22 illustrates a graph of profiles of pressure in the inflatable chambers 326, 326', 326" where the pre-fill steps for the inflatable chambers begin at different times (sequentially), and where during the pre-fill steps the inflatable chambers are inflated to different (gradient) pre-fill pressures. The profiles of pressure in the ankle, calf, and thigh chambers 326, 326', 326" are represented by curves A3, C3, T3, respectively. The pre-fill steps of the inflation phases for the inflatable chambers 326, 326', 326" have respective durations T31, T31', T31" (e.g., about 3, 2, and 1.5 seconds), during which the pressure increases in each of the inflatable chambers to the respective pre-fill pressures P31, P31', P31" (e.g., about 8, 6, and 4 mmHg). The ankle chamber 326 is inflated to a higher pre-fill pressure than the calf chamber 326', which is inflated to a higher pressure than the thigh chamber 326". The therapeutic steps of the inflation phases begin sequentially and have respective durations T32, T32', T32" (e.g., 2.7, 3, and 5.3 seconds), during which the pressure increases to the respective therapeutic pressures P32, P32', P32" (e.g., about 45, 40, and 30 mmHg).

FIG. 23 illustrates a graph of profiles of pressure in the inflatable chambers 326, 326', 326" where the pre-fill step is used in the inflation phase for the ankle chamber 326 only. The profiles of pressure in the ankle, calf, and thigh chambers 326, 326', 326" are represented by curves A4, C4, T4, respectively. The pre-fill step for the ankle chamber 326 has a duration T41 (e.g., about 3 seconds), during which the pressure increases in the ankle chamber to the pre-fill pressure P41 (e.g., about 8 mmHg). The therapeutic steps of the inflation phases begin sequentially and have respective durations T42, T42', T42" (e.g., about 2.7, 3, and 5.3 seconds), during which the pressure increases to the respective therapeutic pressures P42, P42', P42" (e.g., about 45, 40, and 30 mmHg).

The flow rates may vary in the example compression cycles illustrated in the graphs described above. The flow rates may be between about 0.25 LPM and 2.0 LPM during the pre-fill steps and between about 0.5 LPM and 5.0 LPM during the therapeutic steps. The flow rates may be expressed as ratios, such as between about 0.25×LPM and 2.0×LPM during the pre-fill steps, and between about 0.5× and 5.0×LPM during the therapeutic steps, in which "X" is an arbitrary constant. Although these ranges overlap, it is understood that the ratio would be chosen such that the pre-fill flow rate would be less than the therapeutic flow rate. For example, the flow rates may be 0.5× during the pre-fill step and 1.5× during the therapeutic step, or the flow rates may be 1.5× during the pre-fill step and 3.0 during the therapeutic step.

In a second inflation phase example, to manage inflation of the inflatable chambers 326, 326', 326" as described above, the storage medium 342B may include instructions for increasing the gas pressure in at least one of the inflatable chambers 326, 326', 326" during the inflation phase in accordance with the following steps: (1) in a first step, increasing the gas pressure in the inflatable chamber 326, 326', 326" to no more than about a predetermined pre-fill pressure by delivering gas from the source of pressurized gas to the inflatable chamber at a maximum pre-fill flow rate of no more than about a predetermined pre-fill flow rate; and (2) in a second step after the first step, increasing the gas pressure in the inflatable chamber 326, 326', 326" to at least a predetermined therapeutic pressure by delivering gas from the source of pressurized gas to the inflatable chamber at a minimum flow rate of at least about a predetermined therapeutic flow-rate. In the first step, the predetermined pre-fill pressure may in one embodiment range from about 1 mmHg to 22 mmHg, and more desirably from about 2 mmHg to 10 mmHg. In the first step, the predetermined pre-fill flow rate may in one embodiment range from about 0.25 LPM to 2.0 LPM (0.25×LPM to 2.0×LPM), and more desirably about 0.5 LPM to 1.0 LPM (0.5×LPM to 1.0×LPM). In the second step, the predetermined therapeutic pressure may in one embodiment range from about 25 mmHg to about 75 mmHg, and more desirably from about 35 mmHg to 65 mmHg. In the second step, the predetermined therapeutic flow rate may in one embodiment range from about 0.5 LPM to about 5.0 LPM (0.5×LPM to 5.0×LPM), and more desirably about 1.0 LPM to 3.0 LPM (1.0×LPM to 3.0×LPM). Although the stated ranges for the pre-fill and therapeutic flow rates overlap, it is understood that the ratio would be chosen such that the pre-fill flow rate would be less than the therapeutic flow rate. For example, the flow rates may be 0.5× during the pre-fill step and 1.5× during the therapeutic step, or the flow rates may be 1.0× during the pre-fill step and 3.0 during the therapeutic step.

The control system 342 may have various types of instructions for increasing the gas pressure in the inflatable chambers 326, 326', 326" during the inflation phase in accordance with the steps of the inflation phase examples outlined above. For example, the control system 342 may have time-based instructions. In other words, using the first step and ankle chamber 326 as an example, the storage medium 342B may have instructions for inflating the ankle chamber 326 at a certain flow rate (e.g., 1.0 LPM) for an amount of time which has been predetermined to increase the gas pressure in the ankle chamber to no more than the predetermined pre-fill pressure. On the other hand, the control system 342 may have pressure-based instructions. In other words, using the first step and ankle chamber 326 again as an example, the storage medium 342B may have instructions for inflating the ankle chamber 326 at a certain flow rate (e.g., 1.0 LPM) until the pressure in the ankle chamber reaches the predetermined pre-fill pressure, as monitored, for example, by the pressure sensor 342C, where the flow rate is predetermined not to achieve the predetermined pre-fill pressure until at least a desired pre-fill time has expired. In summary, the storage medium 342B may have time-based and/or pressure-based instructions for increasing the pressure in the inflatable chambers 326, 326', 326" in accordance with the two steps of the second inflation phase example outlined above without departing from the scope of the present invention. As explained above with respect to the control system 42, the control system 342 may be programmed to execute pressure-based inflation control during the pre-fill step and to execute timing-based inflation control during the therapeutic step, whereby the pressure-based control during the pre-fill step may enable more precise achievement of the desired end of therapeutic phase pressure. It is understood constant or variable flow rates may be used according to the first and second steps above, as long as the flow rates do not exceed the maximum pre-fill flow rate in the first step or fall below the minimum therapeutic flow rate in the second step.

As described above with respect to the control system 42, the control system 342 of this embodiment may be programmed for (the storage media 342B may have instructions for) executing the pre-fill steps of the first and second inflation phase examples outlined above for the inflation phase of every compression cycle or for the inflation phase of selected compression cycles only. For example, the pre-fill steps may only be used when relatively high flow requirements exist. It is understood high flow requirements normally exist in order to achieve desired therapeutic pressure in sufficiently low time to move blood. However, some inflation phases may require higher flow requirements relative to other inflation phases. The control system 342 may be programmed to normally not execute a pre-fill step during the inflation phase and to execute the pre-fill step only when relatively high flow requirements exist. The pressure sensors 342C, 342C', 342C" and the physical characteristic sensors 342D, 342E may be adapted to indicate when relatively high flow requirements exist. The control system 342 may have instructions to execute the first and second steps in response to signals received from one or more of the pressure sensors 342C, 342C, 342C" and physical characteristic sensors 342D, 342E representing the existence of relatively high flow requirements. For example, one of the pressure sensors 342C, 342C', 342C" may indicate to the CPU 342A that the therapeutic pressure is not being achieved in appropriately short time in the respective chamber 326, 326', 326", which may indicate a relatively high flow requirement, in which case the CPU 342A may begin executing a pre-fill step during the inflation phase for subsequent inflation phases for that chamber. In another example, the first physical characteristic sensor 342D may indicate a compression garment 314 connected to the controller 312 has a relatively large inflatable chambers 326, 326', 326", such as a bariatric sleeve, or additional multiple inflatable chambers, requiring relatively high flow for providing a greater volume of gas for achieving peak pressure, in which case the CPU 342A may begin executing a pre-fill step during the inflation phase. The pre-fill steps may be used in other circumstances in which relatively high flow requirements exist. For example, the control system 342 may be set for applying a relatively high therapeutic pressure in one or more of the chambers 326, 326', 326" such that relatively high flow requirements exist, in which case the controller 312 may use a pre-fill step. The CPU 342A may execute the pre-fill step in any one or two or all three of the inflatable chambers 326, 326', 326" in response to high flow requirements for those particular inflatable chambers.

As is now apparent, utilization of a pre-fill step such as those described above permits use of a smaller and/or lighter weight pressurizer 340A and results in less overall impingement noise. The pre-fill step also provides other advantages. The pre-fill step may increase the lifespan of the pressurizer 340A. For example, if a brush-type motor is used on the pressurizer 340A, using a pre-fill step helps to lower arcing that occurs at the brushes. When the pressurizer 340A is first turned on, the current typically spikes and then settles at a lower level. Using a pre-fill step helps to lower the arcing and thus reduces brush wear. Moreover, using a pre-fill step can decrease noise created by the pressurizer motor at the beginning of inflation. Many conventional systems apply the voltage required for therapeutic inflation immediately, which can be jarring because of sudden noise of a pressurizer turning on at high effective voltage. In the pre-fill step of the present disclosure, the pressurizer 340A turns on at a lower effective voltage. The pre-fill step may also lower power consumed by the pressurizer 340A per compression cycle.

In use, the leg sleeve 314 is fluidly connected to the controller 312 and placed on a leg L of a person. The controller 312 is then initiated to cyclically inflate and deflate the leg sleeve 314 to apply cycles of compression, each of which may include an inflation phase which includes a pre-fill step, or some of which may include a pre-fill step.

Figure 24:
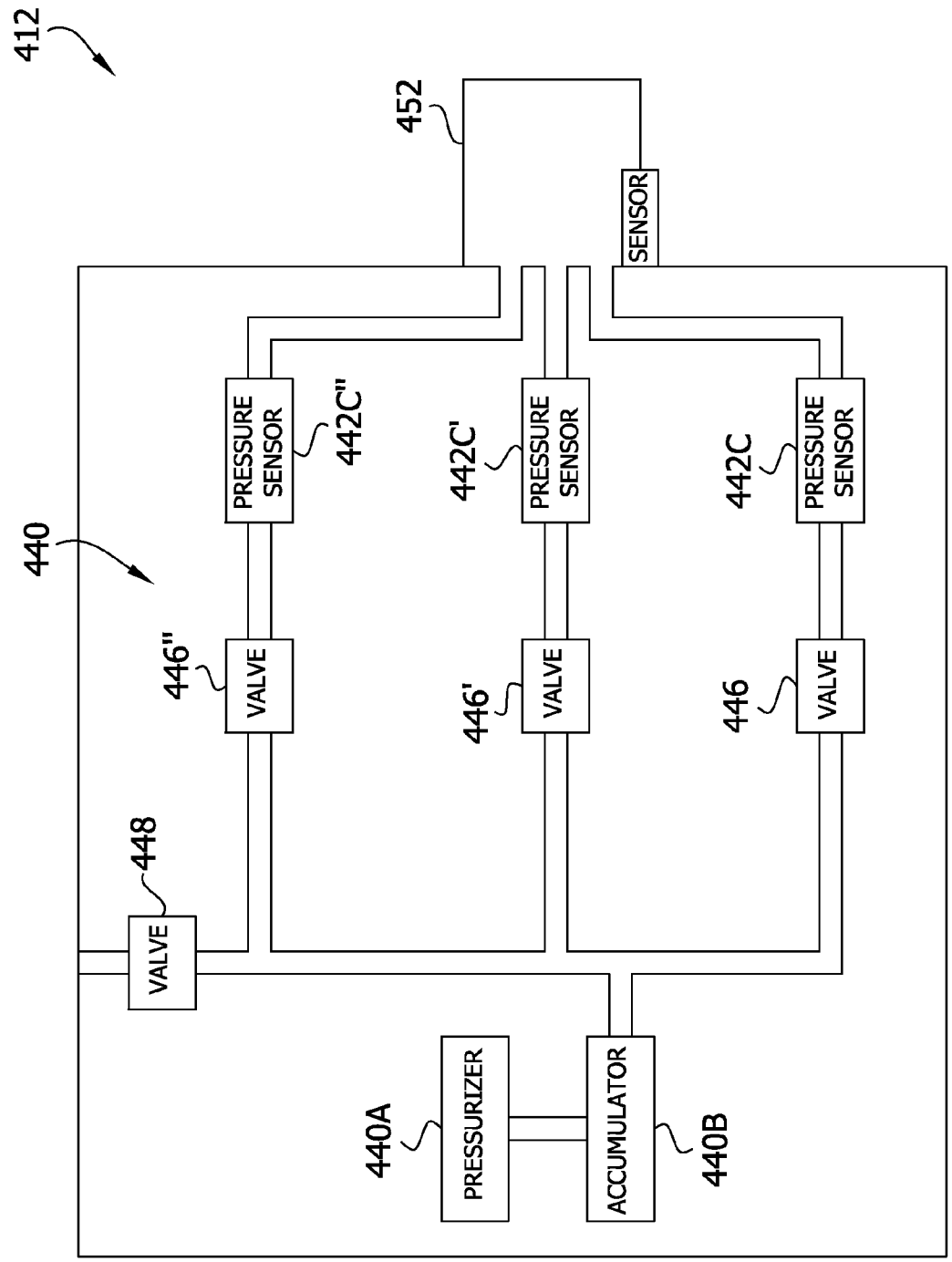
FIG. 24 is a schematic of another embodiment of a controller of the present invention.

FIG. 24 illustrates another embodiment of a controller 412 according to the present invention. The controller is similar to the controller 312 described above, and corresponding parts are indicated by corresponding reference numbers, plus 100. In this embodiment, the controller 412 has a source of pressurized gas 440 which includes a pressurizer 440A, an accumulator 440B, three inflation valves 446, 446', 446", an exhaust valve 448, and a connector 452. The controller 412 also includes three pressure sensors 442C, 442C', 442C". This embodiment of the controller 412 is capable of managing flow of gas into the inflatable chambers 326, 326', 326" as described above. In this embodiment, instead of having pairs of inflation valves in parallel, the controller has variable flow valves 446, 446', 446". For example, the valves 446, 446', 446" may each have two open positions. When in the first open position, the valves 446, 446', 446" may permit flow at a desired pre-fill flow rate, which may be the same or different for each valve, and, when in the second open position, the valves may permit flow at a desired therapeutic flow rate, which may be the same or different for each valve. Thus, controller 412 may be programmed to move the valves 446, 446', 446" to the first open positions to deliver gas to the respective inflatable chambers 326, 326', 326" at the pre-fill flow rate during the first step and move the valves to the second open position to deliver gas to the respective inflatable chambers at the therapeutic flow rate during the second step. The accumulator 440B may be omitted without departing from the scope of the present invention.

Figure 25:
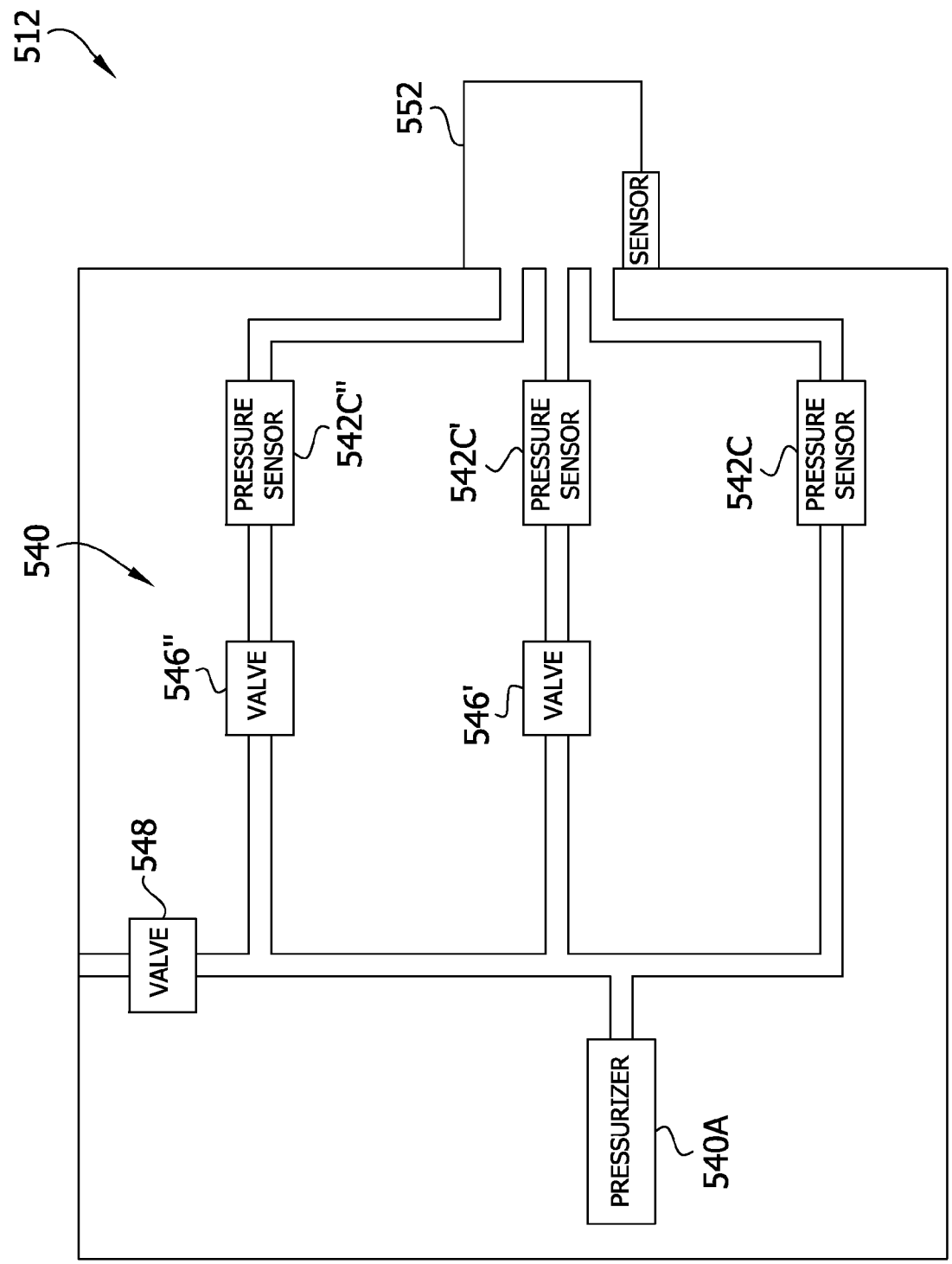
FIG. 25 is a schematic of another embodiment of a controller of the present invention.

FIG. 25 illustrates another embodiment of a controller 512 according to the present invention. The controller is similar to the controller 412 described above, and corresponding parts are indicated by corresponding reference numbers, plus 100. In this embodiment, the controller 512 has a source of pressurized gas 540 which includes a pressurizer 540A, an exhaust valve 548, and a connector 552. The controller 512 also includes pressure sensors 542C, 542C', 542C". This embodiment of the controller 512 is capable of managing flow of gas into the inflatable chamber as described above. In this embodiment, the controller 512 has only two variable flow valves 546', 546", the first being associated with the calf chamber 326', and the second being associated with the thigh chamber 326". The controller 512 may also have a pressurizer 540A in the form of a variable speed pump. For example, the pressurizer 540A may have at least two speeds. At the first speed, the pressurizer 540A may deliver gas flow at the desired pre-fill flow rate for the ankle chamber 326, and, at the second speed, the pressurizer 540A may deliver gas flow at the desired therapeutic flow rate for the ankle chamber 326. The variable flow valves 546', 546" associated with the calf and thigh chambers 326', 326" may each have a closed position and two open positions where the first open positions are adapted for permitting flow at a desired pre-fill flow rate, such as when the pressurizer 540A is operating at the first speed, and the second open positions are adapted for permitting flow at a desired therapeutic flow rate, such as when the pressurizer is operating at the second speed. The valves 546', 546" can be opened at different times such that pre-fill of the thigh chamber 326" can begin after the beginning of pre-inflation of the calf chamber 326', which can begin after the beginning of pre-inflation of the ankle chamber 326. Thus, controller 512 may be programmed to operate the pressurizer 540A and valves 546', 546" to deliver gas to the inflatable chambers 326, 326', 326" at respective pre-fill flow rates, during the first step, and deliver gas to the inflatable chambers at the respective therapeutic flow rates, during the second step. Alternatively, the valves 546', 546" may have single open positions, instead of being variable flow valves, in which case the controller 512 would be capable of managing flow of gas into the inflatable chambers 326, 326', 326" according to some of the methods described above.

Figure 26:
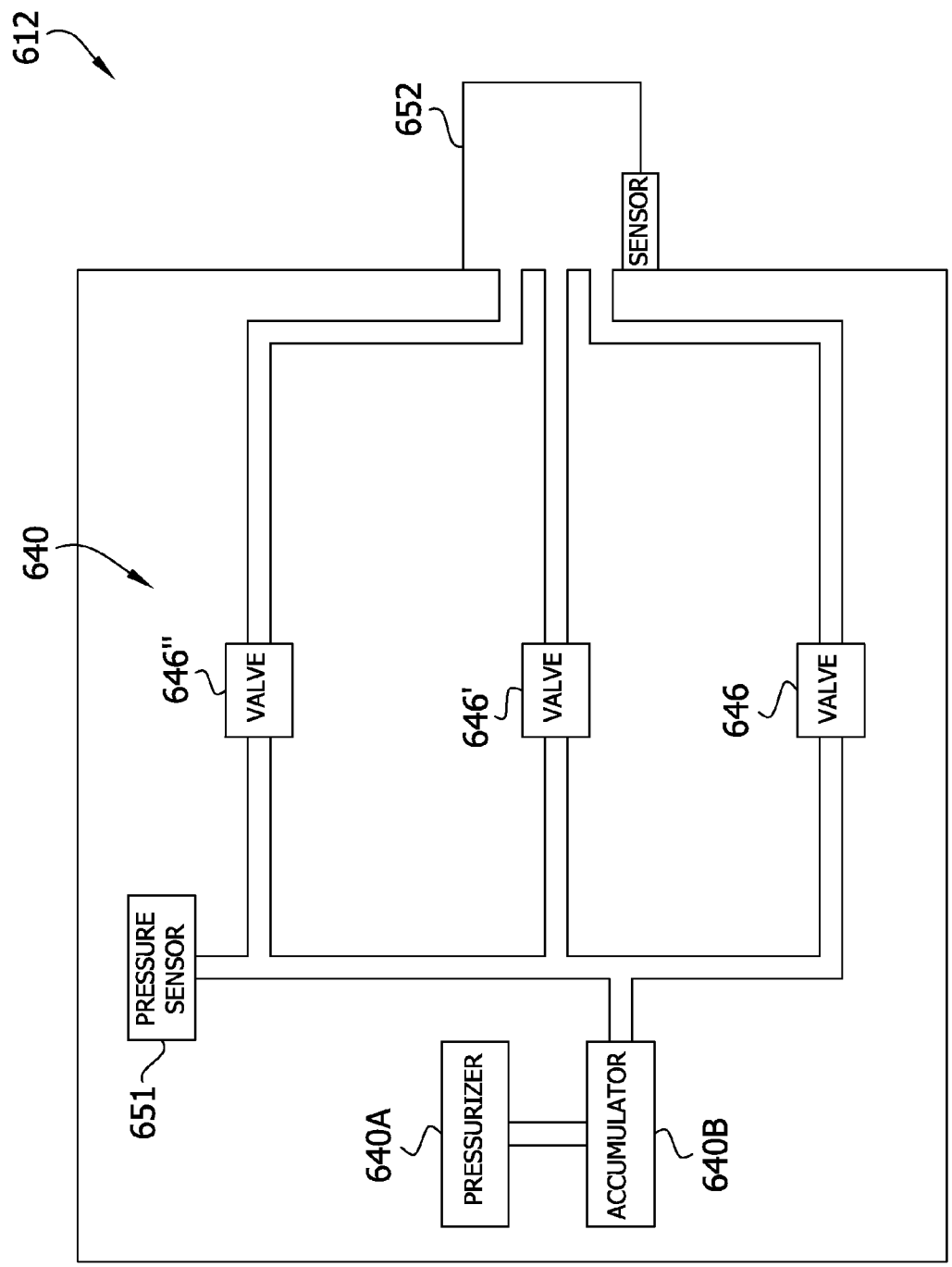
FIG. 26 is a schematic of another embodiment of a controller of the present invention.

FIG. 26 illustrates another embodiment of a controller 612 according to the present invention. The controller is similar to the controller 312 described above, and corresponding parts are indicated by corresponding reference numbers, plus 300. The controller 612 is also particularly similar to controller 412 described above. The controller 612 has a source of pressurized gas 640 which includes a pressurizer 640A, an accumulator 640B, three inflation valves 646, 646', 646", and a connector 652. Instead of having pressure sensors downstream of the inflation valves 646, 646', 646", for example, like the sensors 442C, 442C', 442C" of the controller 412, the controller 612 has a single pressure sensor 651 provided in the common manifold upstream from the inflation valves 646, 646', 646". This exemplary embodiment of the controller 612 is capable of managing flow of gas into the inflatable chambers 326, 326', 326" as described above. To control flow at desired pre-fill and therapeutic flow rates, the valves 646, 646', 646" may be variable flow valves and/or the flow output from the accumulator 640B or pressurizer 640A may be electronically controlled. The accumulator 640B may be omitted without departing from the scope of the present invention.

Having described the invention in detail, it will be apparent that modifications and variations are possible without departing from the scope of the invention defined in the appended claims.

When introducing elements of the present invention or the preferred embodiments(s) thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A controller for use with a compression garment for imparting compression therapy on a body part of a person, the compression garment including at least one inflatable chamber and a port permitting inflation and deflation of the at least one inflatable chamber, the controller including:
   a source of pressurized gas operatively connectable in fluid communication with the at least one inflatable chamber of the compression garment, the source of pressurized gas being adapted for selectively pressurizing the at least one inflatable chamber by increasing gas pressure in the at least one inflatable chamber to provide compression therapy to the body part; and
   a control system operatively connected to the source of pressurized gas and adapted for controlling operation of the source of pressurized gas, the control system including a tangible storage medium having instructions for executing successive compression cycles to impart intermittent compression therapy to the body part, each compression cycle including an inflation phase during which the control system directs pressurized gas to the at least one inflatable chamber and a vent phase after the inflation phase during which the control system permits gas to vent from the at least one inflatable chamber, the control system having instructions to execute at least one of the inflation phases in accordance with the following steps:
   in a first step, increasing the gas pressure in the at least one inflatable chamber to no more than about 20 mmHg in no less than about 0.5 seconds; and
   in a second step after the first step, increasing the gas pressure in the at least one inflatable chamber to at least about 120 mmHg in no more than about 2 seconds.

2. A controller as set forth in claim 1 wherein, in the first step, increasing the gas pressure in the at least one inflatable chamber to no more than about 20 mmHg comprises increasing the gas pressure in the at least one inflatable chamber to between about 2 mmHg to about 20 mmHg.

3. A controller as set forth in claim 1 wherein, in the second step, increasing the gas pressure in the at least one inflatable chamber to at least about 120 mmHg comprises increasing the gas pressure in the at least one inflatable chamber to between about 120 mmHg to about 210 mmHg.

4. A controller as set forth in claim 1 in combination with the compression garment, the compression garment being a foot cuff adapted for application to a foot of the person and for applying efficacious intermittent compression therapy to the foot.

5. A controller as set forth in claim 1 wherein the source of pressurized gas includes first and second valves in parallel, the control system having instructions to, in the first step, deliver gas through the first valve to the at least one inflatable chamber and, in the second step, deliver gas through the second valve to the at least one inflatable chamber.

6. A controller as set forth in claim 1 wherein the source of pressurized gas includes a valve having first and second valve positions, the control system having instructions to, in the first step, deliver gas through the valve in the first valve position to the at least one inflatable chamber and, in the second step, deliver gas through the valve in the second valve position to the at least one inflatable chamber.

7. A controller as set forth in claim 1 wherein the source of pressurized gas includes a variable speed pressurizer, the control system having instructions to, in the first step, operate the pressurizer at a first speed to deliver gas to the at least one inflatable chamber and, in the second step, operate the pressurizer at a second speed greater than the first speed to deliver gas to the at least one inflatable chamber.

8. A controller as set forth in claim 1 wherein the control system has instructions for executing the first and second steps for the inflation phase of selected compression cycles only when high flow requirements exist.

9. A controller as set forth in claim 1 wherein the control system has instructions for executing pressure-based inflation control during the first step and for executing timing-based inflation control during the second step.

10. A controller for use with a compression garment for imparting compression therapy on a body part of a person, the compression garment including at least one inflatable chamber and a port permitting inflation and deflation of the at least one inflatable chamber, the controller including:
- a source of pressurized gas operatively connectable in fluid communication with the inflatable chamber of the compression garment, the source of pressurized gas being adapted for selectively pressurizing the at least one inflatable chamber by increasing gas pressure in the at least one inflatable chamber to provide compression therapy to the body part; and
- a control system operatively connected to the source of pressurized gas and adapted for controlling operation of the source of pressurized gas, the control system including a tangible storage medium having instructions for executing successive compression cycles to impart intermittent compression therapy to the body part, each compression cycle including an inflation phase during which the control system directs pressurized gas to the at least one inflatable chamber and a vent phase after the inflation phase during which the control system permits gas to vent from the at least one inflatable chamber, the control system having instructions to execute at least one of the inflation phases in accordance with the following steps:
- in a first step, increasing the gas pressure in the at least one inflatable chamber to no more than about 10 mmHg in no less than about 1.5 seconds; and
- in a second step after the first step, increasing the gas pressure in the at least one inflatable chamber to at least about 35 mmHg in no more than about 4 seconds.

11. A controller as set forth in claim 10 wherein, in the first step, increasing the gas pressure in the at least one inflatable chamber to no more than about 10 mmHg comprises increasing the gas pressure in the at least one inflatable chamber to between about 2 mmHg to about 10 mmHg.

12. A controller as set forth in claim 10 wherein, in the second step, increasing the gas pressure in the at least one inflatable chamber to at least about 35 mmHg comprises increasing the gas pressure in the at least one inflatable chamber to between about 35 mmHg to about 65 mmHg.

13. A controller as set forth in claim 10 in combination with the compression garment, the compression garment being a leg sleeve adapted for application to at least a portion of a leg of the person and for applying efficacious intermittent compression therapy to the leg.

14. A controller as set forth in claim 10 wherein the at least one inflatable chamber includes a first inflatable chamber and a second inflatable chamber, the control system having instructions to execute both of the first and second steps with respect to each of the first and second inflatable chambers.

15. A controller as set forth in claim 14 wherein the control system has instructions to increase the gas pressure in the first inflatable chamber in the first step to a first maximum pressure, and the control system has instructions to increase the gas pressure in the second inflatable chamber in the first step to a second maximum pressure less than the first maximum pressure.

16. A controller as set forth in claim 14 wherein the control system has instructions to increase the gas pressure in the first inflatable chamber in the second step to a first minimum pressure, and the control system has instructions to increase the gas pressure in the second inflatable chamber in the second step to a second minimum pressure less than the first minimum pressure.

17. A controller as set forth in claim 14 wherein the control system has instructions to begin executing the first step for the first inflatable chamber before beginning to execute the first step for the second inflatable chamber.

18. A controller as set forth in claim 14 wherein the control system has instructions to begin executing the second step for the first inflatable chamber before beginning to execute the second step for the second inflatable chamber.

19. A controller as set forth in claim 10 wherein the source of pressurized gas includes a variable speed pressurizer, the control system having instructions to, in the first step, operate the pressurizer at a first speed to deliver gas to the at least one inflatable chamber and, in the second step, operate the pressurizer at a second speed greater than the first speed to deliver gas to the at least one inflatable chamber.

20. A controller as set forth in claim 10 wherein the control system has instructions for executing the first and second steps for the inflation phase of selected compression cycles only when high flow requirements exist.

21. A controller as set forth in claim 10 wherein the control system has instructions for executing pressure-based inflation control during the first step and for executing timing-based inflation control during the second step.

* * * * *